(12) United States Patent
McCary et al.

(10) Patent No.: US 9,498,377 B2
(45) Date of Patent: Nov. 22, 2016

(54) VIBRATING SURGICAL DEVICE FOR REMOVAL OF VITREOUS AND OTHER TISSUE

(71) Applicants: Brian D. McCary, Saint Louis, MO (US); Toh Seng Goh, Wildwood, MO (US); James Taylor Perkins, Saint Charles, MO (US)

(72) Inventors: Brian D. McCary, Saint Louis, MO (US); Toh Seng Goh, Wildwood, MO (US); James Taylor Perkins, Saint Charles, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 457 days.

(21) Appl. No.: 14/020,386

(22) Filed: Sep. 6, 2013

(65) Prior Publication Data

US 2014/0074013 A1 Mar. 13, 2014

Related U.S. Application Data

(60) Provisional application No. 61/698,411, filed on Sep. 7, 2012.

(51) Int. Cl.
*A61F 9/007* (2006.01)
*A61M 1/00* (2006.01)
(52) U.S. Cl.
CPC ........... *A61F 9/00745* (2013.01); *A61M 1/008* (2013.01)
(58) Field of Classification Search
CPC ............... A61F 9/007; A61F 9/00736; A61F 9/00745; A61F 9/00781; A61F 2009/0087; A61F 2009/0887; A61F 2009/00887; A61M 1/0058; A61M 1/008; A61M 37/0092; A61M 17/32; A61M 17/320068; A61M 17/320072; A61M 17/320076; A61M 17/32008; A61M 17/320092
See application file for complete search history.

(56) References Cited

U.S. PATENT DOCUMENTS

| 3,693,613 | A | * | 9/1972 | Kelman | A61F 9/00745 |
| | | | | | 137/115.03 |
| 3,805,787 | A | | 4/1974 | Banko | 128/276 |
| 3,941,122 | A | | 3/1976 | Jones | 128/24 A |
| 4,531,934 | A | | 7/1985 | Kossovsky et al. | 604/22 |

(Continued)

FOREIGN PATENT DOCUMENTS

GB 2118045 10/1983

OTHER PUBLICATIONS

International Search Report and Written Opinion for PCT/US2013/058533 Date: Jan. 9, 2014 pp. 16.

(Continued)

*Primary Examiner* — Imani Hayman
*Assistant Examiner* — James D Ponton
(74) *Attorney, Agent, or Firm* — Michael L. Smith

(57) ABSTRACT

An ophthalmic surgical device (10) includes a housing (12) having a distal end (14) and a proximal end (16). A cannula (18) is attached to the housing distal end (14) and has a distal tip (20) with at least one port (22) in communication with a lumen (19) extending through the cannula (18) and in communication with an aspiration path (24) in the housing (12). A vibration source (26) is held within the housing (12) for vibrating the distal tip (20) for assisting in vitreous and other tissue removal. An aspiration source (152) connected to the aspiration path (24) for applying a negative pressure to the lumen (19) and the at least one port (22) for removing fluids and the vitreous and other tissue from the eye. The vibration source (26) and the aspiration source (152) together create a periodic bi-directional flow of tissue through the port (22) without creating cavitation externally of the distal tip (20).

21 Claims, 11 Drawing Sheets

(56) References Cited

U.S. PATENT DOCUMENTS

| | | | |
|---|---|---|---|
| 4,634,420 A | 1/1987 | Spinosa et al. | 604/22 |
| 4,989,583 A | 2/1991 | Hood | |
| 6,126,629 A | 10/2000 | Perkins | 604/22 |
| 6,299,591 B1 | 10/2001 | Banko | 604/22 |
| 2006/0253056 A1* | 11/2006 | Kadziauskas | A61F 9/00745 602/22 |
| 2007/0255196 A1 | 11/2007 | Wuchinich | 604/22 |
| 2010/0191176 A1 | 7/2010 | Ho et al. | |
| 2012/0041358 A1 | 2/2012 | Mann et al. | |
| 2012/0157912 A1 | 6/2012 | Sorensen et al. | |

OTHER PUBLICATIONS

International Preliminary Report on Patentability for PCT/US2013/058533 Date: Mar. 10, 2015 pp. 9.

Leitgeb, et al. (1979) "Ultrasonic Vitrectomy an Alternative Technique to Presently Used Mechanical Procedures" Archives of Clinical and Experimental Ophthalmology, vol. 209, pp. 263-268.

European Search Report for EP13835117.6 Date: Apr. 29, 2016 pp. 9.

* cited by examiner

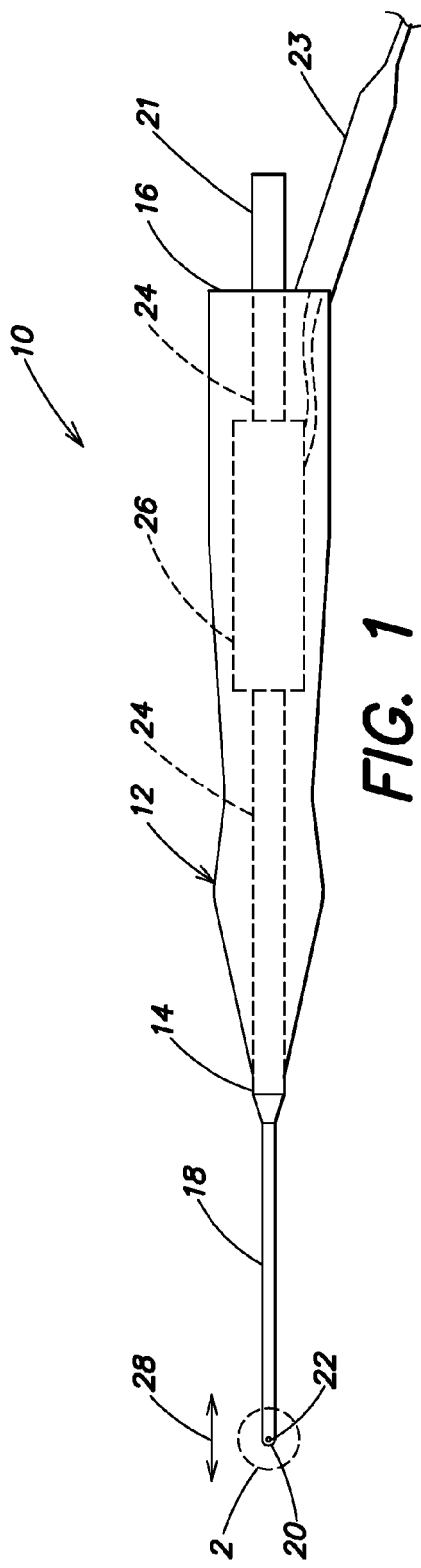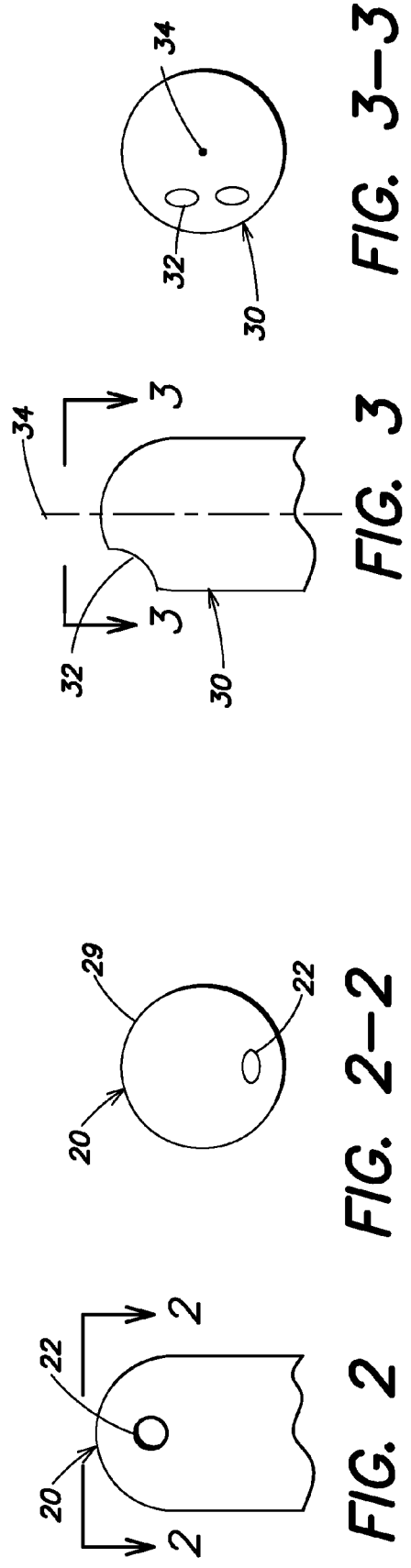

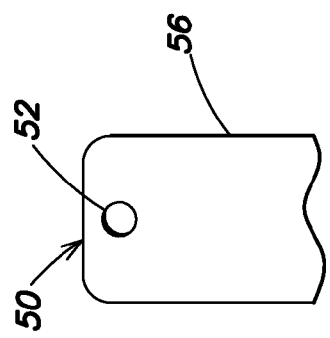
FIG. 5
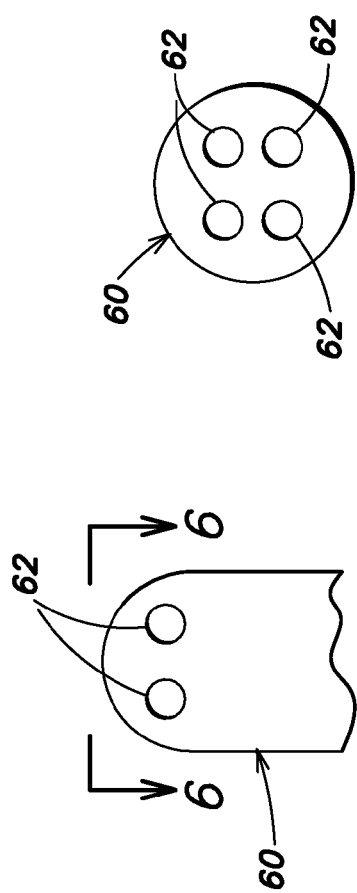
FIG. 6-6
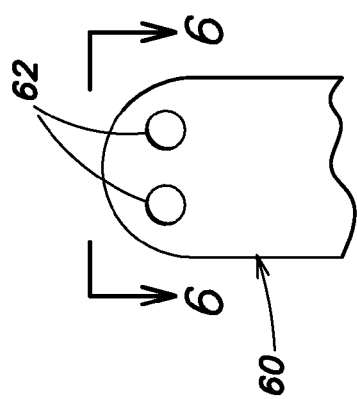
FIG. 6
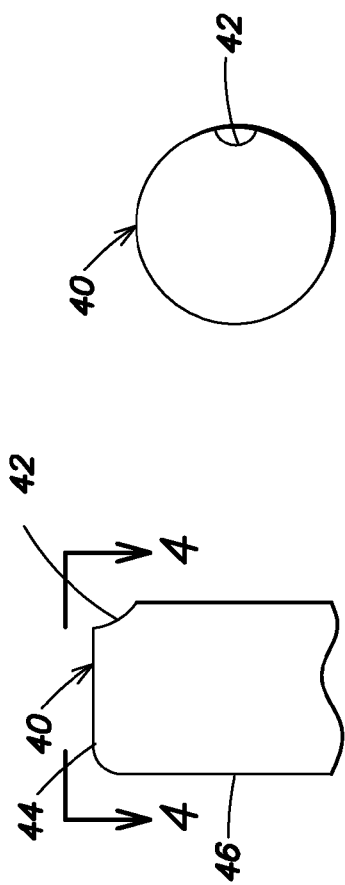
FIG. 4-4
FIG. 4

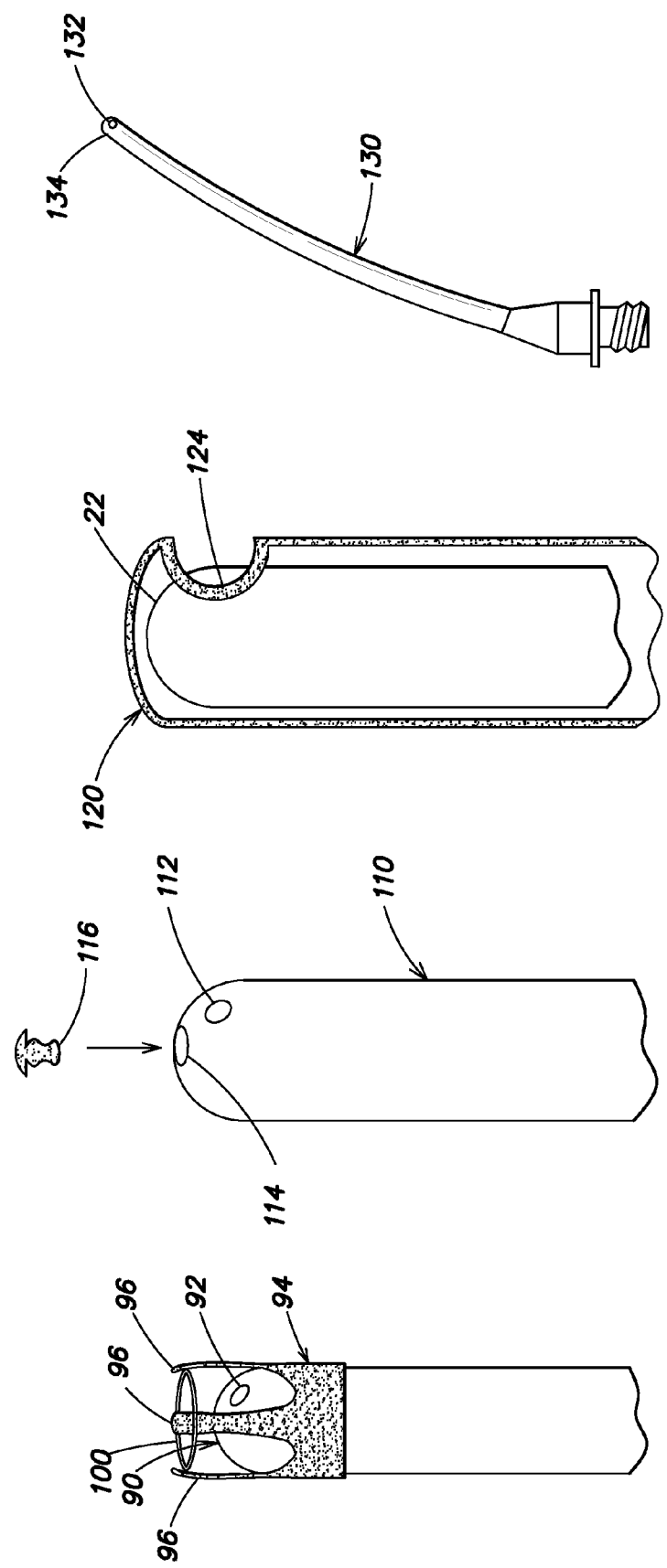

VIBRATING SURGICAL DEVICE FOR REMOVAL OF VITREOUS AND OTHER TISSUE

BACKGROUND

1. Field

The present embodiment relates to an ophthalmic surgical device for the removal of vitreous and other tissue from a patient's eye and, more particularly, to an ophthalmic surgical device that vibrates a cannula with at least one port to disrupt and aspirate vitreous and other tissue from the eye.

2. Description of the Related Art

Vitrectomy cutters (or simply vit cutters) are ophthalmic medical device accessories indicated for use in removing the vitreous humour (often referred to within ophthalmology as "vitreous" or "vit") from the posterior segment of the eye, which lies between the lens and the retina. Sometimes vitreous is removed because it is contaminated with materials that degrade vision (e.g., blood from ruptured vessels, or other cell material, referred to as vitreous floaters, that create spots in the visual field). Other times vitreous is removed to provide surgical access to structures on or near the retina. Also, vitreous is removed to relieve tension exerted on the retina and other structures of the eye.

Vitreous is about 98% to 99% water, but it is bound together with vitrosin. Vitrosin is a "network of collagen type II fibers with the glycosaminoglycan hyaluronic acid" (taken from http://en.wikipedia.org/wiki/Vitreous_humour). Vitreous has a soft jelly consistency and a viscosity two to four times higher than water. The vitreous fibers or strands are anchored to the vitreous membrane (or hyaloid membrane) which rests, in part, next to the retina—pulling on the vitreous membrane can cause optical distortions or even damage to the retina as the vitreous membrane pulls away from the retina. From a fluid dynamic perspective, vitreous may be treated as being thixotropic, exhibiting shear thinning, and as a ground substance, because it is a water based substance containing glycosaminoglycans. Thus, vitreous is an extracellular material in the body classified as thixotropic (see Wikipedia.org for Ground Substance and Thixotropy).

The long collagen fibers create a gelatinous consistency and prevent the vitreous from being aspirated out of the posterior section directly (without prior disruption), in at least three ways. First, the vitreous fibers pull along enough material to prevent vitreous from being drawn into a small hole directly via vacuum aspiration. That is, a small portion will get drawn into the hole, pulling along a larger portion which will not fit through the hole, thereby clogging it. Second, even if, by using a large enough hole and a strong enough vacuum, some vitreous was successfully pulled into the aspirating device, the sticky nature of the vitreous would grab an inner wall of the aspirating device, reducing flow rates below surgically desirable levels. Third, even if a continuous flow were established for a short period of time, the ends of the vitreous strands not yet pulled through the hole will continue to pull material toward them, eventually pulling on and damaging other structures such as the hyaloid membrane or the retina; this is colloquially referred to as "traction" by retinal surgeons. A surgeon will not attempt to passively aspirate the vitreous directly without some form of dissection or disruption if they feel the risk of injury is high enough. For instance, when there is a dropped lens fragment into the posterior segment during surgery, it is common that a vitrectomy (removal of the vitreous) will be done before the lens fragment is removed via phacoemulsification; this is to eliminate the dangers of traction that could occur if phacoemulsification were attempted in vitreous.

Various amounts of vitreous may be removed depending on the disease state being treated. Vitreous is typically removed from the center of the globe to provide access to various areas around the posterior surface of the eye. Vitreous is removed from areas that the surgeon needs to access for therapeutic reasons—for instance, to provide safe direct access to membranes that cover and obscure specific retinal regions. Vitreous is also removed from areas the surgeon identifies as necessary for prevention of future damage to the retina from traction or pulling. In these last two instances, the surgeon will want to remove as much vitreous as possible from specific areas that may be close to the retina.

In most instances, access to the vitreous is gained through the sclera. In some instances, referred to as vitreous prolapse, the posterior wall of the capsular bag holding the lens is ruptured during cataract surgery using ultrasonic phacoemulsification (phaco). In these cases, vitreous in the anterior segment and some vitreous from the anterior portion of the posterior segment may be removed through a corneal entry. It is current clinical practice that a separate vitrectomy device must be used to remove vitreous, instead of the ultrasonic phacoemulsification (phaco) device. If the surgeon attempts to remove the vitreous with either the ultrasonic device using the lens removal tip or an irrigation/aspiration handpiece using the capsule polishing tip, the handpiece needles become clogged by the sticky vitreous and generate traction on the elements in the posterior section of the eye (for the reasons noted above) and become ineffective. It is generally acknowledged in the industry that vitreous cannot be removed from the anterior chamber using a phaco device with a standard tip.

Many patents relating to ultrasound describe breaking ocular tissue in general and lens tissue specifically into fragments or pieces. When considering removal of the lens, describing it as slurry of broken lens fragments mixed with the irrigation fluid provides a fairly accurate model. Given the stringy, sticky, gelatinous nature of the vitreous, this is a less accurate description of the tissue.

In light of the above, a primary design objective of devices for vitreous removal is to break up the vitreous strands, permitting aspiration into a cutter, improving flow through the cutter, and minimizing traction outside the cutter. An additional objective is to minimize the distance between the aspiration port and the end of the device, so that, as long as the low traction target is achieved, vitreous can be removed from regions as close to the retina as possible.

Clinically, the user wishes to achieve five objectives: Remove the vitreous quickly, enter the eye through as small a wound as possible, avoid mechanical damage to the retina from traction or direct cutting, minimize the infusion pressure in the eye, and maintain a stable and positive pressure in the eye. Slow removal of vitreous means longer surgical times, which are stressful for the patient and the patient's eye. Large wounds require stitches across the wound for closure, potentially causing discomfort and optical distortion. Mechanical retinal damage may result in blind spots or chronic vision degradation. High infusion pressures may restrict blood flow to the retina, potentially causing permanent damage to the retina. Fluctuations in intraocular pressure may cause tissue to move into the mouth of the cutter inadvertently, or cause the eye to collapse momentarily. Furthermore, it is possible for bubbles to form at the tip of an ultrasonic cannula when brought into contact with vitreous thereby obscuring vision of the surgical site and adversely affecting the fluidics within the eye. These bubbles, commonly referred to as cavitation, also may damage tissue not intended to be damaged.

These objectives may conflict with each other. In general, tissue aspiration paths must get bigger to speed up vitreous removal; larger aspiration paths, in turn, require larger wounds to insert a cannula, and require higher infusion pressures to support water flow into the eye to keep the intraocular pressure stable. Low infusion pressures provide less safety margin for intraocular pressure fluctuation. A further complicating factor is that vitreous flow for a given pressure differential is generally lower than water flow; and vitreous and water are hard to distinguish visually during surgery, as they are both transparent. The infusion pressure must be set high enough to keep the chamber stable if a tissue cutter's mouth gets into water, or the aspiration vacuum must be set at a low level, minimizing vitreous flow and risking clogging of the tissue cutter. Therefore, it would be desirable to provide a surgical device that allows use of an infusion pressure near normal physiological intraocular pressure levels and still achieve satisfactory vitreous flow through a small lumen while maintaining stable pressure in the eye during surgery.

There have been patents and scientific articles that mention removing vitreous with an ultrasonic device but none have taught how to safely and reliably remove vitreous without traction during surgery.

U.S. Pat. No. 3,805,787 by Banko, discloses removing vitreous with an ultrasonic device. The device includes a shield to confine the ultrasonic energy and provide a safety factor by keeping tissue not to be removed away from the ultrasonic probe, such as protecting the retina. There is no discussion regarding traction of vitreous during removal.

U.S. Pat. No. 3,941,122 by Jones, teaches removing vitreous gels from a physically small, high frequency source, preferably pulsed. The frequency of operation is "on the order of at least 90-100 MHz", considerably higher than conventional 20 to 60 kHz frequencies employed in standard ophthalmic microsurgical systems. Furthermore, the transducer is identified as being located in the radiating tip itself. There is no discussion regarding traction of vitreous during removal.

U.S. Pat. No. 4,531,934 by Kossovsky et al., teaches fragmenting and aspirating ocular tissue, including vitreous, using ultrasound and a needle with a single opening at one end with a diameter substantially less than the diameter of the axial bore of the needle. It includes a "transverse end wall portion . . . opening and bore . . . joined together . . . to create a vacuum to aspirate the ocular tissue", or aspiration without assistance of an aspiration pump, which could result in unacceptably low flow rates. There is no discussion regarding traction of vitreous during removal.

U.S. Pat. No. 4,634,420 by Spinosa et al., relates primarily to an ultrasonic system with an improved removable sheath device for delivery of treatment fluid. Reference to use on vitreous is mentioned. There is no discussion regarding traction of vitreous during removal.

U.S. Pat. No. 6,126,629 by Perkins, discloses a phacoemulsification needle with multiple ports, including an axial port, i.e. a port on the apex of the distal tip, which is safe near the posterior capsule so that vitreous prolapse does not occur. There is no discussion regarding traction of vitreous during removal.

U.S. Pat. No. 6,299,591 by Banko, describes a phacoemulsification instrument, including several embodiments of needles with different geometrical tips and aspiration ports. The different tip designs are for concentrating the ultrasonic energy as desired. There is no discussion regarding traction of vitreous during removal.

US 2007/0255196 by Wuchinich, describes an ultrasonically vibrated solid tip surrounded by a stationary sheath for liquefaction of vitreous. There is no discussion regarding traction of vitreous during removal.

Studies have been published on the use of ultrasound in vitreous, without simultaneous irrigation and aspiration. For instance, in *Ultrasonic Vitrectomy—an Alternative Technique to Presently Used Mechanical Procedures* (Lietgeb, Schuy, and Zirm in *Graefes Archives of Clinical and Experimental Ophthalmology*, volume 209, pages 263-268, 1979) the authors used a 2 mm diameter probe at 60 kHz with an unknown stroke located in the middle of the posterior chamber to liquefy bovine vitreous, and measured the diameter of the liquefied regions around the probe's distal tip. However, no attempt was made to aspirate the vitreous out of the chamber through the device. There is no discussion of traction of vitreous during removal.

Mechanical vit cutters having an inner cutter that is movable relative to an outer cutter are well known and are essentially the only type of vit cutter used. Virtually all mechanical vit cutters are of the guillotine-type with an axially reciprocating inner cutter. There are however, examples in the prior art of inner cutters that rotate or oscillate back-and-forth across a port on the outer cutter. The oscillating cutters are not used because of potential traction problems from uncut vitreous ("spooling") that could cause damage to the retina. In all cases, mechanical vit cutters rely on aspiration to pull vitreous into the cutter port and a reliable scissors-type contact between the inner and outer cutters is required to prevent traction. Typically, pneumatic drives have been used to create the axial inner needle motion; electric drive designs have also been proposed or marketed using motor driven cams, voice coil, solenoids, or low frequency non-resonant piezoelectric actuators. David Wuchinich has proposed a version on his website where the inner needle is driven by a piezo-electric element in a resonant transducer. Despite the differences in drive mechanisms, all of these devices consist of a stationary outer needle with a port and a moving inner needle.

Recently, the frequency of the cutting action of mechanical vit cutters has been increased and the period between cuts has decreased to reduce the overall size of the pieces of cut strands. Cut rates have advanced from 600 CPM (100 msec per cut cycle) to 5,000 CPM (12 msec per cut cycle) and there are active efforts to increase the cut rate to 10,000 CPM (6 msec per cut cycle). The ultimate maximum cut rate will be limited at some point, by the reciprocating mass and by the volumes of air that must be moved back and forth in the pneumatic devices and the motor requirements in electrical devices.

Necessarily, all mechanical vit cutters with needle pair designs include two needles, an outer needle and an inner needle. The aspiration path is routed through the inner needle, and the geometry of the aspiration path is determined, in part, by the inner needle inner diameter (ID). Because the inner needle must move relatively freely inside the outer needle, the effective separation between the inner cutter OD and the aspiration path OD must be two tube wall thicknesses plus some air gap. Ophthalmic surgical instrumentation has been getting smaller, to permit use of smaller incisions, which leak less, heal faster, do not require sutures, require less preparation time, and induce fewer optical aberrations. However, because of this trend, there is user interest in making the OD of the outer cutter smaller. Since (within the basic model for flow in a tube) resistance is proportional to the fourth power of the tube diameter, the use of a second, smaller inner tube to provide the aspiration path limits the aspiration rate by increasing the flow resistance and decreasing the flow rate.

Because the mouth of the outer needle's port must be large enough for a reasonable amount of intact vitreous to be pulled in past the outer needle wall so that it can get trapped and cut by the inner needle and the outer port edge, some of the pieces of vitreous may have a cross sectional area about the same size as or larger than the inner diameter of the outer needle. Therefore, the cut pieces of vitreous are necessarily larger than the aspiration path defined by the ID of the inner needle. This means that the vitreous pieces will drag the inner needle walls and may, from time to time, jam together as they flow up the tube. This increases the flow resistance and the likelihood of clogs, while also decreasing the effective flow rate.

In order to cut effectively, the forward edge of the moving inner needle must extend past the forward edge of the port in the stationary outer needle, while staying pressed hard against it. Because of the desire for both complete cutting of the vitreous to minimize traction, and for the forward-most possible position of the port, designers and manufacturers find themselves balancing the likelihood of an occasional incomplete cut (because the needle end fails to pass the port end) against the inability to cut close to the retina (because the port is located further back from the distal end to provide more room for the inner needle to drive past the end of the port). All mechanical vit cutters rely on some level of interference between the inner needle and the outer needle due to bending or displacement of the inner needle; this interference adds drag, which slows down the inner needle, and makes higher cut rates harder to achieve.

High speed video of vitreous being cut by guillotine cutters has shown that, as the inner needle passes over the port and squeezes the vitreous against the leading outer port edge, the vit cutter pulls on the vitreous outside the port, moving it a distance equal to about the port mouth size, which is typically around 0.015" (381 µm). This creates traction (pulling on the vitreous outside the port beyond the natural flow of vitreous to the port) during each cut, even during perfect cuts.

Flow measurements have shown that the flow rate of water through the current mechanical vit cutters is much higher than the flow rate of vitreous through the same cutters at the same vacuum levels and actuation rates. This indicates that the flow resistance of the vitreous is higher than the flow resistance of water, which has two effects. It makes the overall vitrectomy time longer, and it causes abrupt changes in irrigation flow into the eye as the cutter moves between water and vitreous, and back again. These abrupt flow changes require higher infusion pressures to manage the intraocular pressure, and potentially could cause damage to the structures in the eye.

As noted, surgeons would like the port to be located as close to the end of the cutter as possible, to facilitate removal of vitreous close to membranes that are close to the retina. However, in conventional mechanical vit cutters, the designer must leave space between the forward edge of the port and the end of the outer needle, so that the inner needle has room to pass by it, accounting for all assembly variances and tolerances. This means the forward edge of the cutter port may be located about 0.008" to 0.015" (200 to 380 µm) from the end of the outer needle.

Although partially effective, all the prior art vitreous removal devices fail to fully realize the end goals of small wound size, high flow, and low traction.

BRIEF DESCRIPTION OF THE DRAWINGS

The drawings described herein are for illustrative purposes only of selected embodiments and not all possible implementations, and are not intended to limit the scope of the present disclosure.

FIG. 1 is an elevation of a device of one example embodiment;
FIG. 2 is a partial elevation of FIG. 1 of dashed circle 2;
FIG. 2-2 is an elevation of FIG. 2 taken along line 2-2;
FIG. 3 is a partial elevation of an alternate example of FIG. 2;
FIG. 3-3 is an elevation of FIG. 3 taken along line 3-3;
FIG. 4 is a partial elevation of an another alternate example of FIG. 2;
FIG. 4-4 is an elevation of FIG. 4 taken along line 4-4;
FIG. 5 is a partial elevation of a yet another alternate example of FIG. 2;
FIG. 6 is a partial elevation of a still another alternate example of FIG. 2;
FIG. 6-6 is an elevation of FIG. 6 taken along line 6-6;
FIG. 10 is a partial elevation of another example of a cannula of the example device;
FIG. 11 is a partial elevation of another example of a cannula of the example device;
FIG. 12 is a partial elevation of an alternate example of a cannula of the example device;
FIG. 13 an elevation of an example curved cannula of the example device.

Corresponding reference numerals indicate corresponding parts throughout the several views of the drawings.

SUMMARY

Figure 7:
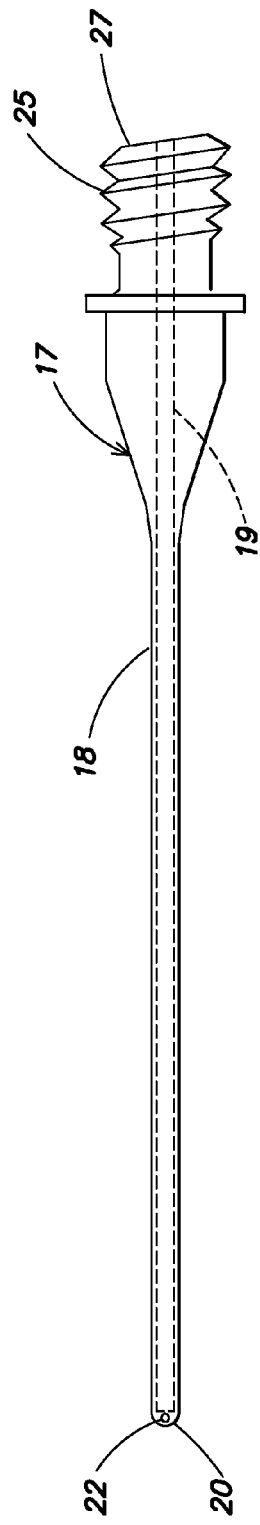
FIG. 7 is a an elevation of a cannula example to be used with the example device.

This section provides a general summary of the disclosure, and is not a comprehensive disclosure of its full scope or all of its features.

Some example embodiments may include an ophthalmic surgical device comprising a housing having a distal end and a proximal end. A cannula is attached to the housing distal end and has a distal tip with at least one port in communication with a lumen extending through the cannula. The lumen is in communication with an aspiration path in the housing. Also, a cross-sectional area of the port is less than a cross-sectional area of the lumen. The ophthalmic surgical device further includes a vibration source held within the housing for vibrating the distal tip of the cannula for assisting in vitreous and other tissue removal from a patient's eye. An aspiration source is connected to the aspiration path for applying a negative pressure to the lumen and the at least one port for removing fluids and the vitreous and other tissue from the eye. The vibration source and the aspiration source together create a periodic bi-directional flow of tissue through the port without creating cavitation externally of the distal tip.

Other example embodiments disclose a cannula for attachment to a surgical instrument capable of vibrating the cannula. The surgical instrument also includes an aspiration path. The cannula has a shaft with a length sufficient to extend across an eye's posterior segment without a proximal portion of the cannula or a distal portion of the surgical instrument contacting an entry-site alignment device. At least one port is formed adjacent a cannula distal tip and to a side of a central axis of the cannula. The port is in communication with a lumen extending through the cannula for communication with the aspiration path. A cross-sectional area of the at least one port is at least one third or less compared to a cross-sectional area of the lumen.

Further example embodiments disclose an ophthalmic surgical kit comprising a first entry site alignment device, an infusion cannula attached to a length of tubing, and a second entry site alignment device for receiving a tissue extraction device. The infusion cannula is for insertion into the first entry site alignment device and the tubing is for attachment to a source of infusion fluid. The first entry site alignment device has a larger diameter lumen than a lumen diameter of the second entry site alignment device.

Another example embodiment discloses an ophthalmic surgical kit comprising a plurality of entry site alignment devices and a plurality of infusion cannulas attached to a length of tubing. Each of the infusion cannulas are for insertion into one of the plurality of entry site alignment devices and the tubing is for attachment to a source of infusion fluid. Another of the plurality of entry site alignment devices is for receiving a tissue extraction device. The plurality of infusion cannulas provide more cross-sectional area for infusion fluid than an aspiration cross-sectional area of a port of the tissue extraction device.

Another example embodiment discloses an ophthalmic surgical system comprises a vitreous cannula attached to a surgical instrument for vibrating the vitreous cannula. The vitreous cannula has a distal tip with at least one port in communication with a lumen extending through the vitreous cannula to a proximal end of the vitreous cannula. The lumen communicates with an aspiration path in the surgical instrument and a cross-sectional area of the port is less than a cross-sectional area of the lumen. Vitreous and other tissue are removed from an eye when the vitreous cannula is vibrated such that a periodic bi-directional flow of tissue is created through the port. An infusion fluid source is connected to an infusion cannula. An aspiration source is attached to the surgical instrument aspiration path for aspirating the vitreous and other tissue from the eye. A plurality of entry site alignment devices for insertion into the eye are for receiving at least the infusion cannula and the vitreous cannula.

Further areas of applicability will become apparent from the description provided herein. The description and specific examples in this summary are intended for purposes of illustration only and are not intended to limit the scope of the present disclosure.

DETAILED DESCRIPTION

Example embodiments will now be described more fully with reference to the drawings.

FIG. 1 is an elevation of an ophthalmic surgical device 10 according to one example embodiment. Device 10 includes a housing 12 having a distal end 14 and a proximal end 16. A cannula 18 is attached to the housing distal end 14. The cannula 18 has a distal tip 20 with at least one port 22 in communication with a lumen (not shown in FIG. 1) extending through the cannula 18 and in communication with an aspiration path 24 in the housing 12. A vibration source 26 is held within the housing 12 for vibrating the distal tip 20 of the cannula 18 for assisting in vitreous and other tissue removal from a patient's eye. An aspiration source (not shown in FIG. 1) is connected to aspiration path 24, via tube connector 21, for applying a negative pressure to the lumen and the at least one port 22 for removing fluids and the vitreous and other tissue from the eye. The vibration source 26 and the aspiration source together create a periodic bi-directional flow of tissue through the port 22, without creating cavitation externally of the distal tip 20. The motion of the tip can cause a periodic bi-directional flow of fluid to pass back and forth through the port or ports, as will be explained in further detail below.

It is noted that device 10 may be cannula 18 attached to a conventional phacoemulsification or fragmentation surgical device which is vibrated as described above. Device 10 may have a vibration source 26 that is piezo-electric, magneto-resistive, or any other vibration mechanism that vibrates cannula sufficiently to disrupt vitreous and other tissue with little or no traction. Vibration source 26 may cause cannula distal tip 20 to vibrate ultrasonically or sonically. If a conventional ultrasonic surgical device is used vibration frequencies of 20-60 kHz are common. Similarly, vibration source 26 may cause the cannula distal tip 20 to vibrate in one or more of a longitudinal manner (as indicated by arrow 28), a torsional manner (about a longitudinal axis of cannula 18), and a transverse manner (a side-to-side or elliptical movement of distal tip 20).

The cannula distal tip may have any of several embodiments, depending on the design and desired performance of the device 10. FIG. 2 through FIG. 6-6 show several examples of cannula distal tips and ports. In addition to the examples shown, the ports can be of varying size and of any desired geometrical shape (e.g. triangular, rectangular, square, oval, octagonal, etc.). The combined cross-sectional area of port 22 or the combine cross-sectional area of multiple ports preferably is less than approximately 75000 square microns ($\mu m^2$). Each port preferably has a smaller cross-sectional area than the lumen of cannula 18 (see FIG. 7 below). More preferably, each port has a cross-sectional area of ⅓ or less compared to the lumen cross-sectional area.

Figure 14:
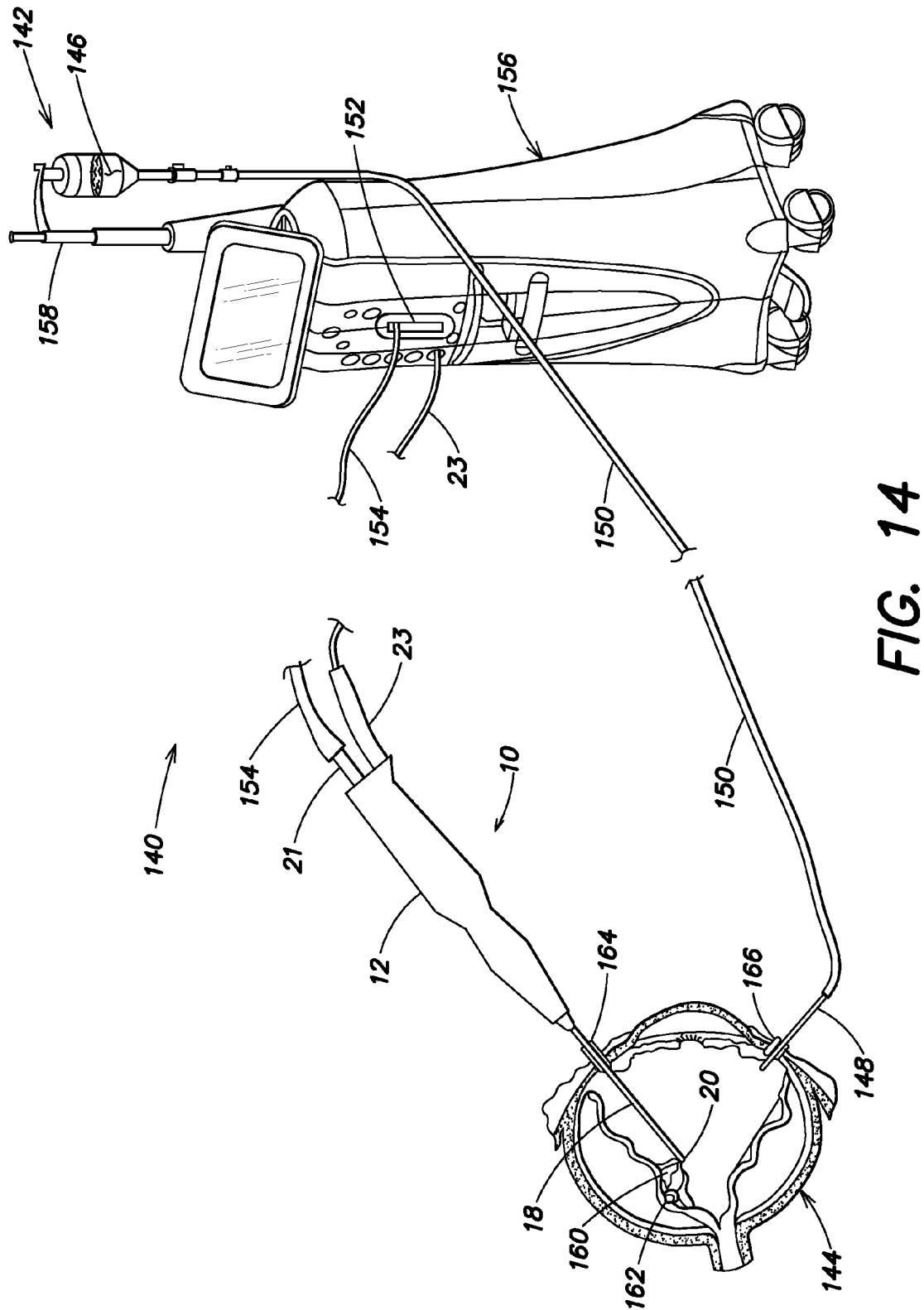
FIG. 14 is a partial perspective view of an example system.

The cannula 18 preferably has a shaft length of 31 to 33 mm from a hub (shown below at 17 in FIG. 7) of the cannula to the distal tip 20, i.e. sufficient length to extend across an eye's posterior segment without a posterior portion of the cannula (the hub) or a distal portion of a surgical instrument (not shown in FIG. 7) contacting an entry-site alignment device (shown in FIG. 14 at 164). The cannula 18 is longer than typical fragmentation needles (typically about 17 mm) and phacoemulsification needles (typically about 14.5 mm). The cannula length or shaft length is defined as the part of the cannula that is generally cylindrical and is the portion of the cannula that will fit within the entry-site alignment device but does not include the tapered portion that is formed from the hub to the generally cylindrical part of the cannula. The cannula preferably has an outer diameter of 20, 23, 25, or even 27 gauge. The port 22 diameters can be formed by plunge EDM (electric discharge machining), laser cutting, or other suitable method and have been formed as small as 0.004" (102 µm) with diameters between 0.006" (152.4 µm) and 0.008" (203.2 µm) presently believed to be preferred, resulting in port cross-sectional areas of less than 35,000 µm$^2$ and less than 20,000 µm$^2$. A port diameter of 127 µm (0.005") results in a cross-sectional area of 12,667 µm$^2$, a diameter of 152.4 µm (0.006") has a cross-sectional area of 18,241 µm$^2$, and a diameter of 203.2 µm (0.008") has a cross-sectional area of 32,429 µm$^2$. Therefore, the port preferably has a diameter that is less than 205 µm, less than 155 µm, or less than 130 µm.

FIGS. 2 and 2-2 have one port 22 formed to a side of the cannula distal tip 20. This side placement of port 22 assists a surgeon to see the port 22 during surgery and to allow a side 29 of the cannula distal tip 20 opposite the side with the port 22 to contact delicate tissue without damage. If a port were to be formed on the axial tip or apex of distal tip 20 it would be impossible for a surgeon to see the port during surgery and unwanted tissue could be disrupted and removed from the eye. The ability to see the tissue around the port is critical to the surgeon for safe treatment. Also, an axial tip port would reduce the effectiveness of creating the desired periodic bi-directional flow by reducing the effective moving cross-sectional area in the distal tip 20, requiring greater vibration power (tip velocity) which, in turn, could increase the possibility of harm to retinal tissue compared to that required by ports formed to the side of the cannula central axis FIGS. 3 and 3-3 show a cannula distal tip 30 with multiple ports 32 in communication with a lumen of the cannula. The multiple ports 32 are formed to a side of a central axis 34 of the cannula.

FIGS. 4 and 4-4 show a cannula with a generally flat distal tip 40 with a port 42 formed is a radiused transition portion 44 between the flat distal tip 40 and a side wall 46. The geometry or form-factor of the distal tip may be of any shape, depending on the method of manufacture and the desired performance of the cannula (e.g. pyramid-shape, rounded (like FIG. 2), square, conical, frusto-conical, etc.).

FIG. 5 is similar to FIG. 4 except flat distal tip 50 has a port 52 in a side wall 56.

FIGS. 6 and 6-6 show a distal tip 60 with multiple ports 62.

FIG. 7 shows cannula 18 with port 22 having a smaller cross-sectional area than lumen 19. Cannula 18 is also shown having a threaded connection 25 at a proximal end 27 for attachment to the device 10, which may be a phacoemulsification surgical instrument. Of course cannula 18 may have other connections such as frictional-fit, quick-connection, or any suitable mechanism for attaching cannula 18 to device 10. In addition, cannula 18 could be machined as a single structure with component parts of vibration source 26, such as a horn (not shown).

FIG. 8 through FIG. 11 show alternate examples of a guard device attached to the cannula and extending beyond the cannula distal tip. The guard devices can be attached by any sufficient method, including adhesive, frictional contact, over-molding, or any other suitable technique. The guard devices are preferably formed of a soft, compliant material, such as silicone or other suitable material. The guard devices serve to protect delicate tissue, such as the retina, from damage.

Figure 8A:
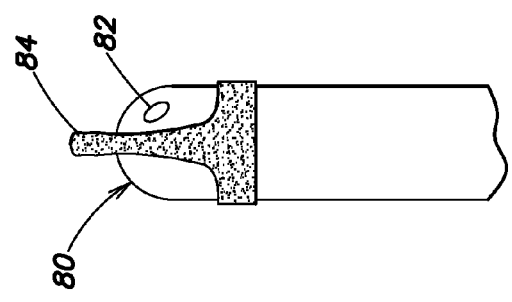
FIG. 8a is a 90 degree rotated view of FIG. 8.
Figure 8:
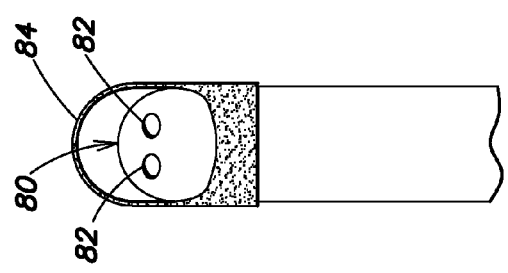
FIG. 8 is a partial elevation of yet another example of a cannula of the example device.

FIG. 8 shows a cannula distal tip 80 with ports 82 and a guard device 84 attached to the cannula and extending beyond the cannula distal tip 80. The distance that guard device 84 extends beyond cannula distal tip 80 depends on the performance of the device, the surgeon's preference, and the margin of safety desired. Guard device 84 may be described as a looped band configuration. The distance may be about 1 mm or less. FIG. 8a shows FIG. 8 rotated 90 degrees.

Figure 9:
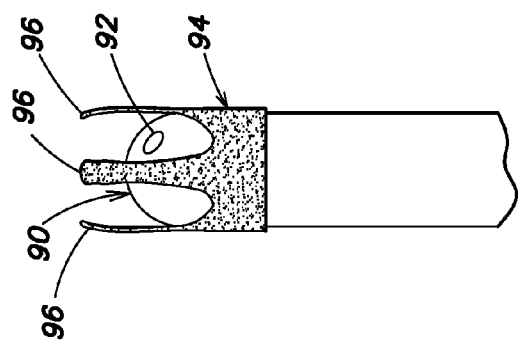
FIG. 9 is a partial elevation of still another example of a cannula of the example device.

FIG. 9 shows a cannula distal tip 90 with port 92 and a guard device 94. Guard device 94 may be described as a plurality of tentacles 96.

FIG. 10 is the same as FIG. 9 with the addition of a reinforcement ring 100 supporting the tentacles 96.

FIG. 11 shows a cannula distal tip 110 with a port 112 and a hole 114 for receiving a plug 116 formed of silicone or other suitable soft, compliant material for protecting delicate tissue that is not to be removed or damaged during a vitrectomy.

FIG. 12 shows a compliant jacket 120 attached to the device 10 (attachment not shown). Jacket 120 surrounds and extends beyond the cannula distal tip 122. The jacket 120 also includes a port 124 proximate the cannula distal tip 22. This jacket is not stationary with the needle, but moves with it.

FIG. 13 shows a curved cannula 130 that may assist the surgeon to see the port 132 of the distal tip 134.

Referring back to FIG. 1, vibration source 26 preferably is capable of vibrating the cannula distal tip 20 sufficiently to remove a lens fragment embedded in the vitreous, which typically will be significantly greater than the vibration needed to remove vitreous. To remove a lens fragment may require ultrasonic vibration. It will be appreciated that the cannula 18 with its relatively small port 22 will emulsify a lens fragment but because the holding force or purchase of the cannula 18 is significantly less than a standard phaco or fragmentation needle, device 10 will be less efficient than a standard fragmentation device with a standard needle. It is believed that vibration source 26 needs to vibrate the cannula distal tip 20 at a velocity amplitude that depends on both the inner lumen area and the average aspiration flow rate. For a 20 gauge ETW (extra-thin wall) tip and a 0.5 ml/min aspiration rate, this would be at least 0.02 meters per second (m/sec). Device 10 also includes an aspiration tube connector 21 for attaching aspiration tubing (not shown) and a power cord 23 for supplying control signals and power to vibration source 26. Cannula 18 is attached to surgical instrument or device 10 that vibrates cannula 18. Cannula 18 has a distal tip 20 with at least one port 22 in communication with lumen 19. Lumen 19 extends through the cannula 18 to a proximal end 27 of the cannula 18 and the lumen 19 communicates with an aspiration path 24 in the surgical instrument 10. Vitreous and other tissue are removed from an eye when the cannula is vibrated such that a periodic bi-directional flow of tissue through the port 22 is created. Some expected target minimum tip velocities as a function of flow and gauge are shown in Table 1 below, as a design example. In Table 1, under the gauge column, E refers to extra-thin wall and U refers to ultra-thin wall.

TABLE 1

Unidirectional Flow Ceiling/Bidirectional Flow Threshold:
Minimum Tip Velocity, m/sec, to get bi-directional flow, Based on Gauge
$V_{tip} > Q_{asp}/Area_{InsideTip}$

| | | Target Aspiration Flow, ml/min | | | | |
|---|---|---|---|---|---|---|
| Gauge | ID Max (m) | 0.5 | 1 | 1.5 | 2 | 2.5 |
| 20E | 0.00072 | 0.020 | 0.040 | 0.061 | 0.081 | 0.101 |
| 23E | 0.00051 | 0.041 | 0.082 | 0.123 | 0.164 | 0.206 |
| 24E | 0.00043 | 0.057 | 0.114 | 0.171 | 0.228 | 0.285 |
| 25E | 0.00038 | 0.073 | 0.146 | 0.219 | 0.292 | 0.365 |
| 26E | 0.00037 | 0.078 | 0.156 | 0.235 | 0.313 | 0.391 |
| 27E | 0.00033 | 0.097 | 0.195 | 0.292 | 0.389 | 0.487 |
| 23U | 0.00056 | 0.034 | 0.068 | 0.102 | 0.136 | 0.170 |
| 24U | 0.00048 | 0.046 | 0.091 | 0.137 | 0.182 | 0.228 |
| 25U | 0.00043 | 0.057 | 0.114 | 0.171 | 0.228 | 0.285 |
| 26U | 0.00039 | 0.068 | 0.137 | 0.205 | 0.274 | 0.342 |
| 27U | 0.00036 | 0.084 | 0.168 | 0.252 | 0.336 | 0.420 |

The peak tip velocity is the peak velocity reached by distal tip 20 caused by the vibration. The peak tip velocity or $V_{TP}$, can be expressed as the tip harmonic velocity at a frequency, f, of vibration. It is well-known to use a value of peak to peak stroke distance ($S_{p-p}$) at a vibration frequency as a metric unit for quantifying vibration output. Therefore, $V_{TP} = S_{p-p} * \pi * f$.

The potential maximum flow velocity of water $V_{water}$ through a port depends on a pressure differential or pressure drop across the port. So in this instance the maximum flow velocity of water through the at least one port 22 can be expressed for a pressure differential between the intraocular pressure of the eye and a pressure within the cannula lumen 19. For there to be aspiration the pressure in the lumen 19 must be less than the intraocular pressure. The intraocular pressure includes the natural pressure in the eye plus any infused fluid into the eye less any fluid aspirated or leaked from the eye. It is noted that in the formulas below the pressure differential is stated as intraocular pressure plus aspiration vacuum value because aspiration is conventionally expressed in terms of a negative pressure below atmospheric pressure, rather than as absolute pressure. For a pressure drop of $\Delta_p$ and an aspiration medium of density $\rho$, if there are no other losses, an infinitesimal volume of water can be accelerated from static to a velocity of $\sqrt{(2 \cdot \Delta_p/\rho)}$. Thus, $V_{water} = \sqrt{(2 \cdot \Delta_p/\rho)}$, where $\Delta_p$=(intraocular pressure+ aspiration vacuum), and $\rho$=density of medium, ~1000 kg/m³ for water and vitreous. $V_{water}$ is expressed in meters per second (m/sec) and may be further modified by a coefficient applied to the $\Delta_p$ term to compensate for losses from the flow through the port. The coefficient is commonly between 0.62 and 0.75.

An average aspiration fluid velocity through a port $V_{flavg}$, depends on the volumetric flow rate F and an area size of the port. So $F = V_{flavg} * N * A_{port}$, where F may be in m³/sec, $V_{flavg}$ is in m/sec, $A_{port}$ is in m², and N is the number of ports. For circular ports the area is of course $\pi * r^2$.

Port 22 or any combination of multiple ports has a holding force of less than 1 gram at 735 mmHg vacuum or less. Because of the small holding force, combined with the limited distal tip velocity, there has been found to be little or no traction when disrupting and aspirating vitreous and other delicate tissue in the back of the eye.

FIG. 14 shows a system 140 that includes additional devices beyond ophthalmic surgical device 10. For instance an infusion fluid source 142 is in communication with the eye 144. A pressure of infusion fluid 146 into the eye 144 forms a part of the intraocular pressure of eye 144. An infusion cannula 148 for insertion into the eye 144 preferably has a cross-sectional area larger than a cross-sectional area of port 22 or any combined cross-sectional area of multiple cannula ports. Infusion cannula 148 communicates with source 142 via infusion tubing 150. An aspiration source 152 is applied to the aspiration path 24, via aspiration tubing 154. Aspiration source 152 applies a negative pressure to the lumen 19 and the port 22 for removing fluids and the vitreous and other tissue from the eye 144. Power cord 23 is connected to a surgical console 156 for controlling vibration source 26. Infusion source 142 is shown as a bottle or bag of balanced-salt solution attached to a pole 158 that moves up and down to increase or decrease the pressure of the fluid 146 flowing into the eye 144. However, infusion source could take other forms such as a pressurized infusion source or a bag that is squeezed to apply the proper infusion pressure, or any other suitable manner of providing infusion fluid into the eye.

FIG. 14 shows device 10 removing vitreous 160 from eye 144 in order to repair retinal rupture 162. Cannula 18 and infusion cannula 148 are shown inserted into eye 144 through entry site alignment (ESA) devices 164 and 166. ESA devices 164 and 166 are known and allow for sutureless surgery, as the ESA devices make incisions small enough to self-seal without the need for sutures. Preferably infusion cannula 148 has a lumen (not shown) that is 23 gauge and the vitreous cannula 18 lumen 19 is 25 gauge or smaller.

FIG. 14 can be described as an ophthalmic surgical system 140. The system 140 includes a vitreous cannula 18 attached to a surgical instrument or device 10 for vibrating the vitreous cannula 18. The vitreous cannula 18 has a distal tip 20 with at least one port (see FIG. 2 thru 6) in communication with a lumen 19 (see FIG. 7) extending through the vitreous cannula 18 to a proximal end 27 of the vitreous cannula 18. The lumen 19 communicates with an aspiration path 24 in the surgical instrument 10. Vitreous 160 and other tissue are removed from the eye 144 when the vitreous cannula 18 is vibrated such that the vibration source and the aspiration source together create a periodic bi-directional flow of tissue through the port without creating cavitation externally of the distal tip. Infusion fluid source 142 is connected to an infusion cannula 148 through infusion tubing 150. Aspiration source 152 is attached to the surgical instrument 10 and aspiration path 24, via connector 21, for aspirating the vitreous 160 and other tissue from the eye 144. A plurality of entry site alignment devices 164, 166 are for insertion into the eye 144 and for receiving at least the infusion cannula 148 and the vitreous cannula 18.

Figure 15:
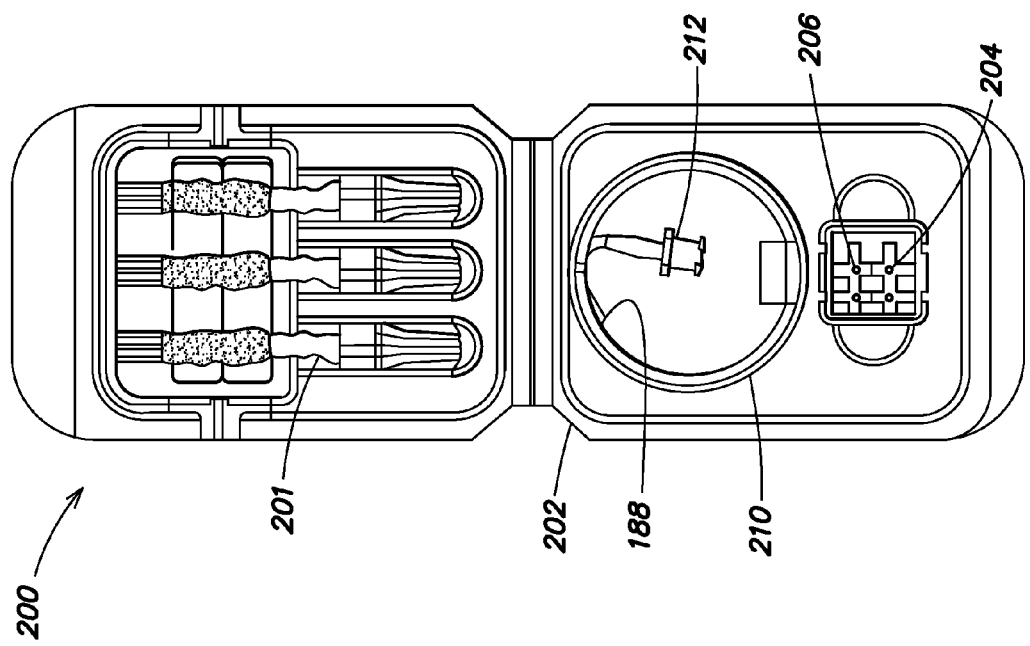
FIG. 15 is an elevation view of an example kit.

FIG. 15 shows an ophthalmic surgical kit 200. Kit 200 may be useful with conventional vitrectomy systems and devices, such as mechanical vit cutters, in addition to the present invention. The current trend towards ever smaller surgical instruments creates a problem of generating enough flow through the vit cutter/removal device. Smaller instrument lumens require higher vacuum levels to generate enough flow to prevent clogging and maintain a sufficient volume of tissue removal. If the size of the infusion cannula and the infusion ESA device is the same as that used for the vit cutter, the infusion cannula may require excessive infusion pressures to maintain the intraocular pressure during surgery. Excessive infusion pressure can lead to tissue damage and fluid jets that obscure the surgical site and create unwanted turbulence in the liquid in the eye. To avoid these problems an infusion cannula with a larger cross-sectional area than the cross-sectional area of the inner diameter of the vit cutter/vitreous removal device can be used. This allows the infusion cannula to provide sufficient infusion fluid volume at safe, low infusion pressures and maintain a stable intraocular pressure.

Figure 16:
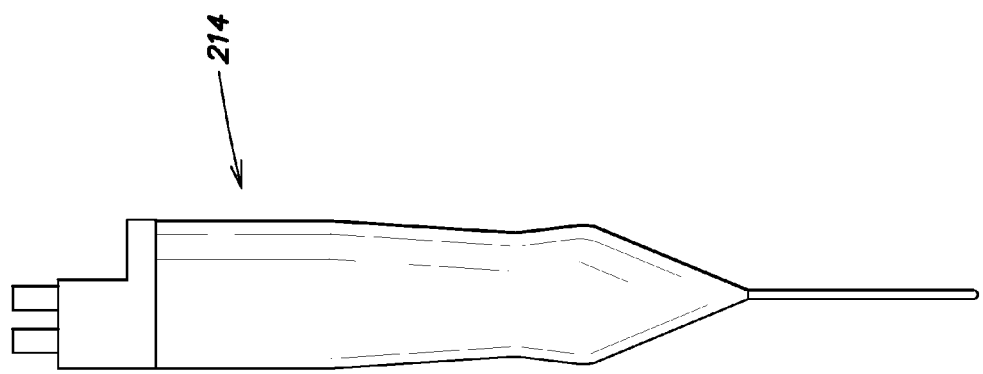
FIG. 16 is an elevation view of an alternate device included in the example kit.

Kit 200 includes a package 202 with a first entry site alignment device 204 and a second entry site alignment device 206. Kit 200 also includes an infusion cannula 188 attached to a length of tubing 210. The cannula 188 is for insertion into the first entry site alignment device 204 and the tubing 210 is for attachment to a source of infusion fluid (not shown and not part of the kit), via a connector 212. The second entry site alignment device 206 is for receiving a tissue extraction device, such as the vibrating surgical instrument 10 described above or a conventional guillotine-type vit cutter 214, as shown in FIG. 16. The first entry site alignment device 204 has a larger diameter lumen than a lumen diameter of the second entry site alignment device 206. The kit 200 may further included the tissue extraction device 214 or 10 for removal of vitreous and other tissue from a patient's eye. The kit 200 may also include a cannula 18 for attachment to a vibrating surgical instrument 10, the cannula 18 having a distal tip 20 with at least one port 22 in communication with a lumen 19 extending through the cannula 18 and in communication with an aspiration path 24 in the housing 12 (as shown in FIG. 7). A plurality of trocars 201 may also be included in kit 200.

In the alternative, rather than the infusion cannula having a lumen larger than the lumen of the tissue extraction device, one could use multiple infusion cannulas of the same or smaller lumen size of the tissue extraction device. The goal is to provide more cross-sectional area for the infusion fluid than aspiration cross-sectional area of the port(s) or lumen of the tissue extraction device.

In consideration of the above, a new vitrectomy device design is proposed that addresses the shortcomings of existing designs. It consists of a single, covered or uncovered, moving outer needle, sans inner needle, with one or more off-axis ports. The port(s) preferably has a cross sectional area less than 70% of the cross sectional area of the inner diameter of the needle (so that any dimensions of remaining intact gelatinous chunks are too small to cause clogging) and a maximum dimension across the port between about 0.003" and 0.012" (75-305 microns), depending on the needle gauge. This could be a single port for to a side of the axis of the cannula, with a diameter less than half the inner diameter of the needle and this will achieve acceptable results.

Additional construction preferences are that the cannula/needle be small enough to pass through either standard wounds in surgery (for instance, OD of 1 mm or less) or entry sight alignment system cannulas (for instance, OD of 0.625 mm or less for 23 gauge systems), and that it be long enough to reach across the eye globe (for instance, a distance from the taper at the end of the hub to the tip of the shaft of 30 mm or more).

As an example of the motion amplitudes and construction dimensions, the port size might be around 0.005" or 127 microns and the minimum wall thickness might be 0.001" or 25 microns; the maximum expected displacement amplitude might be between 5 and 15 microns. As an example of relative velocities, a device with a displacement amplitude of 10 microns and a harmonic operating frequency of 28,500 Hz would have a harmonic velocity amplitude of about 1.8 m/sec; the particle velocity through four 0.005" (125 micron) diameter holes in the end of the device would be around 1.2 m/sec for flow rates of 3.5 ml/min, consistent with desirable flow rates of water through similar 23 gauge devices.

A number of minor variations on the example embodiments can be made. These include the total number of holes, the diameter of the holes, the inner and outer contour of the distal tip, the material used to make the needle, the processes used to make the needle (which could be machined monolithically or fabricated from components, and could include drilling or EDM or other processes for forming the holes), the overall length, inner and outer diameters, operating frequencies, and continuous or pulsed operation.

As part of the example embodiments, certain drive control modes may be envisioned. For instance, some users may want to grasp or peel anatomical features such as membranes with the tip. Because the cutter only requires low vacuum levels and has small holes, the grasping power of the tip may be considerably lower than with conventional cutters. Therefore, one control mode of the device involves automatically applying high levels of vacuum when ultrasonic power is not being commanded, but dropping the commanded aspiration vacuum level down once ultrasonic power is applied.

Alternative directions of tip motion can be contemplated. For instance, because the holes in the end of the tip are slightly off center, torsional action of the tip may result in the sides of the holes disrupting and liquefying the vitreous in a manner similar to the disruption that takes place with longitudinal motion. Torsional action of the port may create bi-directional flow by pushing fluid from the side region of the port directly to the outside and inside of the needle. Likewise, a slight lateral or transverse motion may achieve the same effect. In this case, bidirectional flow may result in the alternating pressure and vacuum zones that will be created in front of the port as the needle moves along the axis of the port, or induced low pressure zones created by high fluid velocities across the face of the port if the needle is moving parallel to the face of the port.

An alternative description of an example embodiment may be that the surgical device of the present disclosure may achieve higher flow rates than a conventional guillotine vit cutter at the same vacuum levels.

The example embodiments improve flow through multiple mechanisms, including increasing the area within the needle available for the aspiration path for tissue that has made it through the ports, eliminating blockage of the aspiration port by an inner needle during a portion of the aspiration cycle, the application of high shear stresses along the wall of the smallest aspiration path diameters, causing shear thinning in the thixotropic vitreous, and breaking up the vitreous into smaller pieces (through mechanisms that will be discussed shortly). Each of these mechanisms is described in greater detail in the paragraphs which follow.

The example embodiments have only one needle, not two needles, as in mechanical vit cutters. By eliminating the inner needle, flow through the needle at a given pressure differential across the needle may be increased by a factor of two to four for the same outer diameter of the outer needle. Classical analysis of non-turbulent flow resistance through a long tube is known to be related to the equation $1/\text{Length}*\text{Diameter}^4$. Typical conventional mechanical vitrectomy devices have an aspiration lumen at least 30 mm, long enough to reach from the entry point at the side of the eye across the globe to points on the other side of the eye. Diameters of some typical needle material combinations are shown in Table 2, below, in units of 0.001" (for conversion to metric multiply numbers in table by 25.4 microns).

TABLE 2

| Outer Needle or Vitrectomy Needle | | | | Inner Needle, Guillotine Only | | | |
|---|---|---|---|---|---|---|---|
| Gauge | Wall | OD | ID | Gauge | Wall | OD | ID |
| 23 MTW | 1 | 25.0-25.5 | 22.5-24.0 | 25 MTW | 1 | 20.0-20.5 | 17.5-18.5 |
| 25 MTW | 1 | 20.0-20.5 | 17.5-18.5 | 27 MTW | 1 | 16.0-16.5 | 14.0-15.0 |
| 27 MTW | 1 | 16.0-16.5 | 14.0-15.0 | 29 MTW | 1 | 13.0-13.5 | 11.0-12.0 |
| 23 UTW | 1.5 | 25.0-25.5 | 20.0-22.0 | 26 UTW | 1.5 | 18.0-18.5 | 14.5-15.5 |
| 25 UTW | 1.5 | 20.0-20.5 | 15.5-17.0 | 28 UTW | 1.5 | 14.0-14.5 | 11.0-12.0 |
| 27 UTW | 1.5 | 16.0-16.5 | 13.0-14.0 | 30 UTW | 1.5 | 12.0-12.5 | 9.0-10.0 | where MTW = Micro-Thin Wall; UTW = Ultra-Thin Wall

It can be seen that, for outer needles fitting through a given gauge cannula, eliminating the inner needle may increase the diameter of the aspiration path by 25% to 40%, which translates to decrease in flow resistance of at least $(1-(1/1.25)^4$ which is greater than) 55%. Use of different production methods for the needles, such as machining, may impact this final result.

In addition, the inner needle of a mechanical vit cutter is generally much longer than the minimum distance required to reach across the eye, as it must be attached to a drive mechanism after exiting the outer needle. This contributes to an additional increase in the flow resistance, due to the inverse of the length factor.

In conventional vitrectomy cutters, the inner needle blocks the aspiration port during part of the cut cycle, resulting in a decrease in aspiration. For instance, at a fixed vacuum level, water will flow through a conventional cutter at a rate of about 5 ml/min, with the port continuously open; vitreous flows at a rate of 0 ml/min in the same condition. Once cutting is activated, vitreous flow increases (because the vitreous is now cut into smaller pieces) but water flow decreases, because the cutter aspiration port is now blocked part of the time by the needle. In conventional cutters, minimizing the transit time of the inner needle minimize the period of blockage, thereby increasing the flow through the eye, but shorter transit times typically require higher drive pressures, and as cut rates increase, the relative transit time (the closed duty cycle) inevitably rises. Eliminating this blockage time with the example embodiments maximizes the total time available during the disruption cycle for aspiration.

Thixotropic materials, such as the vitreous, become less viscous when subjected to high shear stresses. Reciprocating the wall of the aspiration path continuously will apply high shear stresses to any vitreous in contact with the wall, causing it to stay liquid, dropping the flow resistance. Once the aspirated tissue moves into the larger diameter aspiration path downstream of the needle, the fluidic resistance of the pathway drops, as does the expected flow velocity, minimizing the impact of fluidic resistance of this portion of the path.

The example embodiments also include features which facilitate the disruption and liquefication of the vitreous; the pieces that result will be smaller than the pieces that result from conventional vitreous dissection. Even if the inner diameter of the aspiration path remained the same, the smaller pieces would result in reduced flow resistance.

Specifically, the hole or pattern of holes at the end of the needle permits only smaller pieces through; by selecting holes substantially smaller than the ID of the aspiration path helps break the material into pieces smaller than the aspiration path cross sectional area. Additionally, hole patterns with multiple holes create one or more webs between the holes that separate individual flow streams (and the strands in those flow streams), separating the vitreous as it comes in. Furthermore, when the end of the needle is displaced rapidly in a harmonic manner at velocities that form bi-directional flow through the port creates local shear stresses that liquefy the thixotropic vitreous. Furthermore, once pulled through the small hole, the minimum aspiration path area through the 25 gauge tube in the cannula is much greater than the port area. Pieces which fit through the port and are disrupted close to the wall will not clump together nor clog on each other.

Moreover, in the process of spreading out in the aspiration lumen after passing through the ports, the material will be subjected to high lateral shear stresses. Thus, during a time period lasting just a couple of harmonic cycles (<0.1 msec), the vitreous tissue will be pulled into the vicinity of the aspiration port, portions of the tissue will be pulled back in a direction opposite to the direction of flow, then pulled in the direction of aspiration flow at velocities greater than the average flow velocity, then spread out thin within the larger aspiration lumen area. The resulting turbulent mix of cyclical stresses disrupts and liquefies the tissue, breaking it into pieces that eliminate traction outside the needle and minimize flow resistance inside the needle.

Furthermore, as inertial jets form at higher port velocities, high lateral shear stresses will be encountered in the port from the simultaneous bidirectional opposing form that form and by the rotational flows that form in the toroidal cells, further breaking up the vitreous and liquefying it.

The discussion immediately above is shown in Table 3 below comparing conventional vit cutter performance against the example embodiments disclosed.

TABLE 3

| Conventional Aspiration Particle velocity | Conventional Cutter peak velocity | Harmonic displacement amplitude, $H_2O$, @ STP | Vitreous harmonic liquefier particle velocity | Vitreous harmonic liquefier velocity amplitude |
|---|---|---|---|---|
| 0.75 m/sec Length of aspirated & cut segment ~9 mm | 0.4 m/sec | 0.37 m/sec | 1.1 m/sec Length of aspirated & cut segment ~0.0662 mm | 3.5 m/sec |

In an acoustic medium, harmonic motion is reciprocating or oscillating motion, where a pressure wave may be transmitted through a medium through the local displacement of particles. It is important to understand that, while the phase front of the pressure wave can travel tremendous distances, the particles in the medium move very little, and in a cyclical fashion, returning to previous locations every oscillation period. The amplitude of the particle motion is determined by the magnitude of the pressure wave passing by the particle in the media; the greater the pressure amplitude of the wave, the greater the displacement amplitude of the particle. The particle velocity can also be described as a harmonic function, and will be the first derivative of the particle displacement amplitude function. This relationship is well understood in acoustics, and one simple guiding equation is:

$P = z_m * u$ where

P=the harmonic pressure function
u=the harmonic particle velocity function, and
$z_m$=a material characteristic known as the acoustic impedance.

It may be appreciated that, at sea level, the pressure amplitude cannot exceed one atmosphere—at amplitudes above this, the negative half of the pressure amplitude, in absolute terms, would drop below absolute vacuum, which is physically impossible. Therefore, as the needle tip moves backward away from the tissue outside it, it will create a near vacuum for a pressure, but cannot create an absolute vacuum. Once the absolute pressure in the vicinity of the tip drops below the vapor pressure of the medium, pockets full of saturated vapor will form at convenient boundaries, limiting further drops in vacuum.

In contrast to harmonic particle motion, aspiration particle velocities are unidirectional. Particle velocities are a function of the actual volumetric flow rate and the aspiration path geometry. Aspiration flow particle velocities can be estimated from the equation V=Q/Area, where V is the average flow velocity across a plane, Q is the volumetric flow rate, and Area is the cross-sectional area of the flow path.

Flow rates between 1.5 and 15 ml/min would be considered desirable from an ophthalmic clinical perspective. If flow rates are too low, the time to remove the vitreous from the globe becomes excessive. If they are too high, fluidic balance in the eye may be compromised, and the surgeon may have difficulty keeping the surgical site stable.

Flow velocities will be highest where the path area is smallest. In conventional vitrectomy devices, this has been within the inner needle. Flow path diameters of devices compatible with standard 23 or 25 gauge entry site alignment system cannulas are determined by the ID of the aspiration needle, which, in conventional devices, will be 0.38 mm at most, down to as small as 0.28 mm in diameter. This results in a range of particle speeds of 0.29 m/sec to 0.54 m/sec at flow rates of 2 ml/min, as a minimum. Higher velocities would result from higher flow rates, and smaller needle path geometries.

For a conventional 23 gauge 5000 CPM (cuts per minute) cutter with desired water flow rates around 3.5 ml/min, it is worth noting that the leading edge of a segment of cut tissue will travel a distance of 6 to 12 mm through the aspiration needle for every cut, with an average particle velocity between about 0.5 and 1.0 m/sec, and a peak particle velocity around twice this. For comparison, the peak inner needle velocity for a 5000 CPM cutter with a total stroke of around 1 mm will be around 0.4 m/sec. Because the needle velocity will be proportional to the stroke, which is proportional to the port size, which is, in part, proportional to the needle gauge, the smaller cutter inner needles may run slightly slower.

However, the inner needle achieves this peak velocity for only a short period of time. The needle accelerates forward from a dead stop in response to increasing air pressure; the resulting velocity function is proportional to the square of time, until the needle hits the forward stop.

For comparison, a prototype 23 monolithic ultrasonic vitrectomy needle with an OD of 0.025" (635 microns), an ID of 0.020" (508 microns), and four 0.005" (127 microns) diameter holes arranged symmetrically at the end for use at 28.5 kHz and harmonic stroke amplitudes of 5 to 15 microns has been constructed. At the same 3.5 ml/min flow rate of a typical mechanical vit cutter, average flow velocities through these four holes would be around 1.1 m/sec. At peak to peak displacement amplitudes of around 10 microns, the peak exchange flow velocity amplitude is around 3.7 m/sec, meaning that it exceeds the aspiration flow velocity for a significant portion of the cycle (greater than 30%), effectively reversing the direction of flow through the port, and, at the same time, moves in the opposite direction for a significant portion of the time. An alternative single 0.005" hole device of otherwise similar construction and drive conditions will result in both higher aspiration flow velocity (3.5 m/s) and peak exchange flow velocity (~10 m/s), still yielding a reversal of flow direction.

The inventive surgical device and needle of this disclosure breaks up vitreous by passing a small volume of fluid (the "exchange bolus") from a generally slowly advancing intake flow rapidly back and forth through a small port such as port 22 of FIG. 1, creating a periodic bi-directional flow of tissue through the port. The periodic bi-directional flow of tissue is similar to the harmonic motion referred to above. The rapid back and forth motion breaks up the tissue through shear forces that develop between the edge of the exchange flow and the center of the exchange flow, and by tension forces between the rapidly moving trailing edge of the exchange bolus and the slow moving leading edge of the advancing intake flow (when the bolus is moving from outside the tip to inside the tip, or normal motion) or trailing edge of the receding exhaust flow (when the bolus is moving from inside the tip to outside the tip, or retrograde motion.) In theory, the greater the velocity of the exchange flow, the greater both types of forces are.

The present device creates the periodic bi-directional flow or exchange bolus by providing a substantially closed tip with a small port, driven at a velocity sufficient to cause bi-directional flow through the port, with an aspiration vacuum applied. The drive velocity of the tip must be sufficient to create the bi-directional flow at the desired aspiration flow level. At some point, the vacuum created inside the tip by the tip velocity reaches a maximum level, and the effect of the tip may be said to be optimized. Tip velocities above those greater than that creating a maximum vacuum will continue to be effective for disrupting the tissue, but may have negative side effects, such as turbulence or tissue injury, and at some point, they begin to generate cavitation outside of the tip. Maintaining the tip drive velocity at a point below a level at which cavitation is created externally of the tip is desired.

Although the invention is described below using a hollow spherical tip, it should be noted that the action of the invention depends only on areas, and not shapes. Hollow hemispherical tips, solid hemispherical tips, and flat ended tips with equivalent inner, outer, and port areas will have similar minimum drive velocities and optimal drive velocities, although the upper cavitation drive velocity limit may depend somewhat on the external tip geometry.

Volumetric flow through the tip consists of two components: a time invariant aspiration flow rate $Q_{asp}$ and a time variant acoustic flow $Q_{acstc}$. The use of the capital letter Q to represent volumetric flow (volume per unit time) is well established in the literature.

$Q_{total}(\text{time})(=Q_T(t))=Q_{asp}+Q_{acstc}(t)=Q_{DF}+Q_{HF}(t)$

The subscript HF denotes bi-directional flow or Harmonic Flow and DF for Direct Flow. It is noted that if $Q_{HF}(t)$ is symmetric, (for instance, $Q_{HF}(t)=Q_{HF0}*\sin(\omega t)$), $Q_T(t)$ will be asymmetric, and the maximum positive value will be greater than the minimum negative value.

$Q_{DF}$ should be selected to be a value high enough to permit the surgeon to get through surgery in a timely manner, but not so high that the eye becomes unstable or requires high static infusion pressures. Surgeons have generally been satisfied with products that permit vitreous aspiration rates of about 1.5 ml/min (between 1 and 2 ml/min) in the center of the eye, and may use lower flow rates as they get close to critical or loose structures, such as the retina. SI units for volumetric flow are $m^3/sec$; 1.5 ml/min is about $2.5\times10^{-8}$ $m^3/sec$, or 0.025 ml/sec, or 25 μl/sec, or 25 $mm^3/sec$. Aspiration is always into the port. Therefore, for sign convention, flows into the tip through port are designated as positive flow and flows out of the tip through the port are negative flow.

Aspiration Velocity $V_{DF}=Q_{DF}/\text{Area}_{port}=Q_{DF}/A_{port}$ $Q_{HF}(t)$ is the volume displaced back and forth through the port by the action of the inner and outer moving surfaces of the tip. Effectively, it is the area of the inner surface normal to the axis of motion multiplied by the velocity of the surface in parallel to the axis of motion. The magnitude of the Q depends on the inner area, the port area and the velocity of the tip, and is influenced by the angle between the port and the axis of motion. The basic equation is:

$$Q_{HF}(t)=Q_{HF0}\sin(\omega t)$$

where $Q_{HF0}$=Velocity of the tip normal to the axis of motion multiplied by the {Inner area of tip normal to the axis of motion−(Area of port multiplied by the cosine of the angle between normal to port and the axis of motion)}=$V_T*(A_{ID}-A_{port}*\text{Cosine}(\phi))$.

Positive flow is, by the convention we established above, flow into the port; negative flow is flow out of the port. Positive flow occurs as the tip moves forward, into the external area, as the outer surface pushes fluid from the front surface of the tip and pulls fluid with the inside of the tip surface.

Aspiration Velocity $V_{HF}(t)=Q_{HF}(t)/A_{port}$, also $Q_{HF}(t)=A_{InsideTip}*V(t)_{tip}$ In a linear state, $Q_{HF}(t)=Q_{HF}*\sin(wt)$; in non-linear states this may not be true.

A needle or device is operating in a unidirectional flow domain (no bi-directional fluid flow through the needle port) when the peak negative value for $V_{HF}(t)$ is less than $V_{DF}$. That is, $V_T(t)=V_{DF}+V_{HF}(t)$ is always positive. Fluid is always flowing into the port, although fluid is speeding up and slowing down. Fluid flow corresponds essentially to the tip passing the midpoint in its forward moving stroke, and fluid flow is a minimum about when the tip passes the midpoint in its backward moving stroke.

Flow is in the unidirectional flow domain when $QDF/A_{InsideTip}>V_{tip}$. Devices and needles operate in this domain for high aspiration rates, small displacement areas, and low tip velocities. Typical phaco needles operate in this domain, because the area inside the tip is zero, (that is, the tip is not closed at all) making the term on the left side of the equation infinitely large. They typically clog if operated in vitreous, confirming this domain is not effective in vitreous. Typical I/A devices and needles operate in this domain, because the tip velocity is zero, making the term on the right side of the equation very small. They typically clog if operated in vitreous, confirming this domain is not effective in vitreous.

A device and needle enters the bi-directional flow domain above the threshold identified above, when the harmonic velocity is just slightly above the aspiration velocity, or average linear velocity. Changes in flow in this domain can be considered linear up to the point where the pressure difference necessary to achieve the velocity into the port from either side is greater than about one to two full atmospheres of pressure. The action of the inner surface moving forward can create up to one atmosphere of vacuum at the outer entrance to the port; the action of the outer surface moving forward at the same time can create positive pressure outside and adjacent the port. The amount of positive pressure generated depends on the outer tip dimensions and the tip velocity.

Flow through the port is limited at the upper end by static flow through an orifice, where $V_{port2}=2\Delta_{Pressure}/\rho$, which can be extended into the time domain: $V_{port}^2(t)=2\Delta_{Pressure}(t)/\rho$. In this case, $\Delta_{Pressure}(t)$ is from the forward moving surface to the outer entrance to the port. It cannot rise much above 1 ATM (103500 Pa) as there can be no greater than 1 ATM vacuum inside the needle at the port, and the peak pressure generated at the outside of the tip can never be greater than the peak vacuum generated inside the needle, and typically less, in linear conditions. Furthermore, note that flow through the port identified above by $V_{port}$ is a combination of the linear flow and the bi-directional exchange flow. When the needle is moving back towards the surgical device, the needle inner surface can generate a pressure necessary to move fluid out of the port. The forward motion case is the limiting case. Furthermore, the maximum bidirectional flow velocity that can be achieved may be less than the theoretical maximum aspiration flow, because of the acoustical and inertial effects.

The device and needle fluidics will be limited when the reactive acoustic pressures that are created by the tip in the vicinity of the port are no longer sufficiently high to pull material through the port at the necessary velocity. At this point, cavitation will start inside the needle, and the reciprocating acoustic flow will start to be limited. This crossover point can be predicted, to an extent, and depends mostly on the tip velocity, with a weak dependence on the tip dimension. Once in the non-linear domain, the bi-directional flow increases more slowly as the tip velocity increases.

$Q_{DF}=V_{tip}*A_{tip}=A_{port}*\sqrt{(2*\text{ATM}/\rho)}-Q_{asp}$

To find a limiting case, the $Q_{asp}$ term is dropped and the equation above simplifies to $V_{tip}=(A_{port}/A_{tip})*\sqrt{(2*\text{ATM}/\rho)}$. The $\sqrt{(2*\text{ATM}/\rho)}$ term is entirely physical constants; at ATM=103500 Pa and ρ=1000 kg/$m^3$ for water, it equals 14.4 m/s. Furthermore, in the case of a round inner area and a round port, the equation for the maximum linear action tip velocity can be further simplified to $V_{tip}=(D_{port}/D_{tipID})^2*14.4$ m/sec. Over a large variation in flow, the limiting velocity does not vary much for the needle sizes considered, supporting the use of the simplified equation for calculating the limit.

Figure 17A:
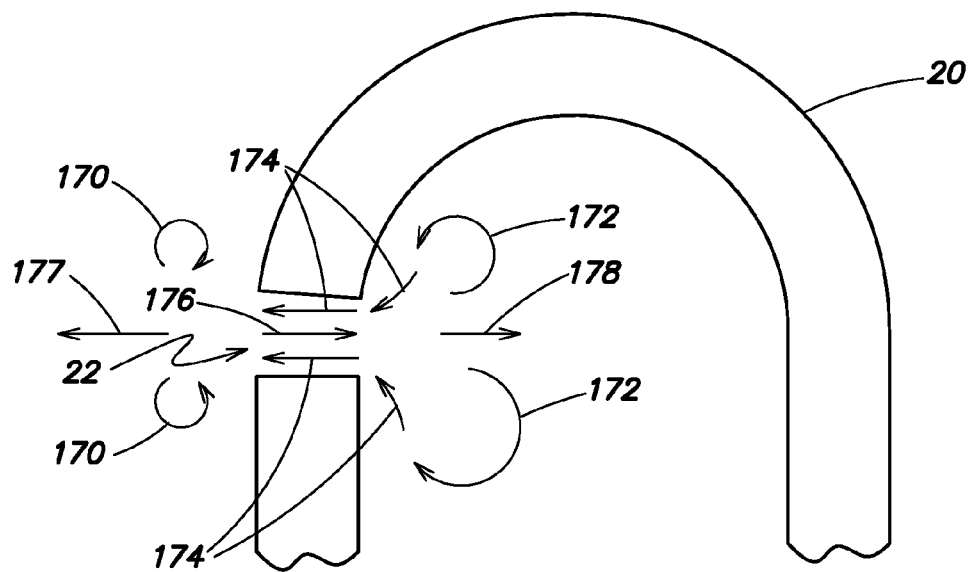
FIGS. 17A-D are partial cut-away views of a cannula illustrating vitreous flow.
Figure 17B:
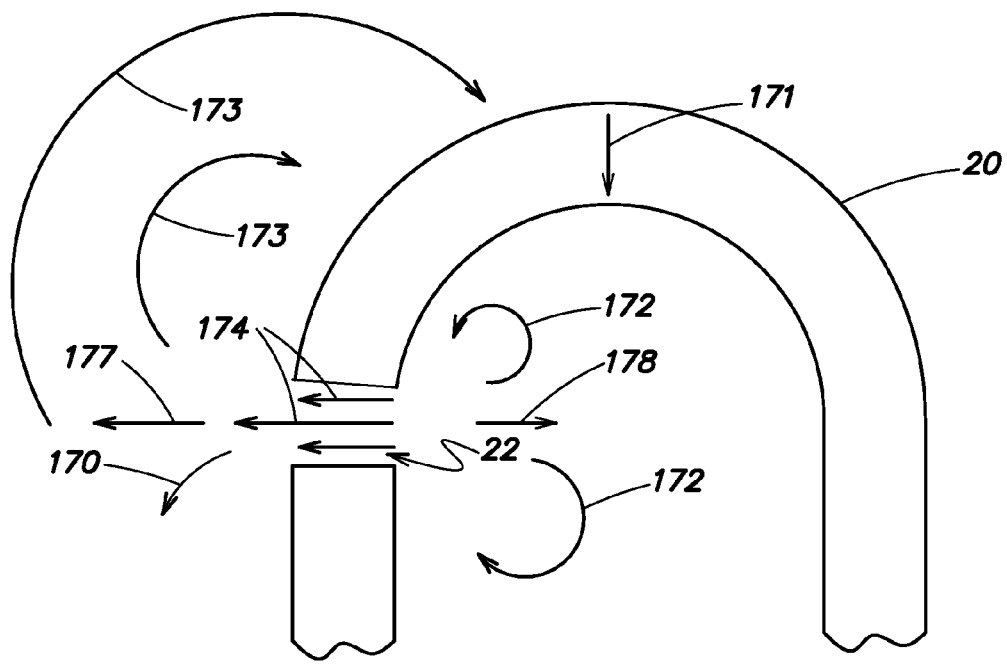
Figure 17C:
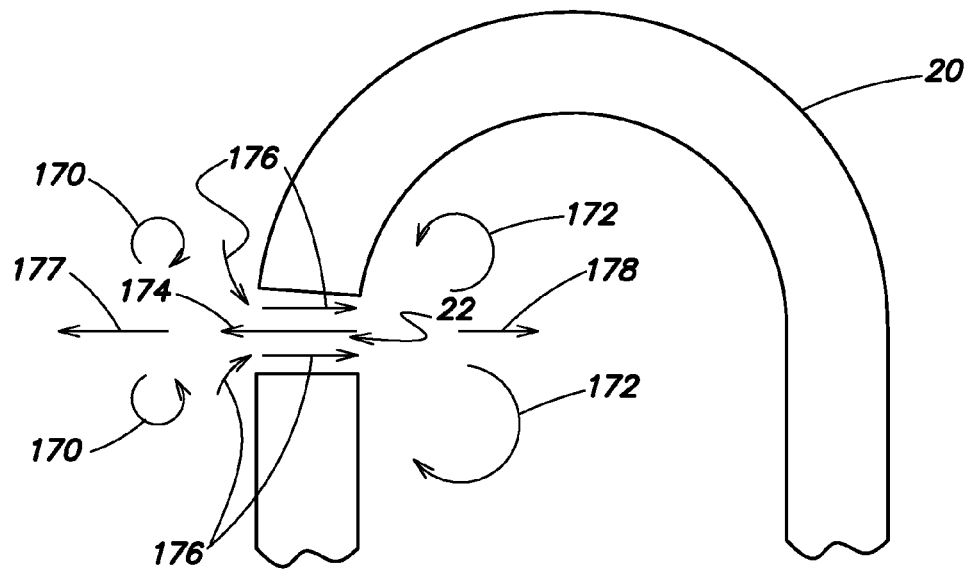
Figure 17D:
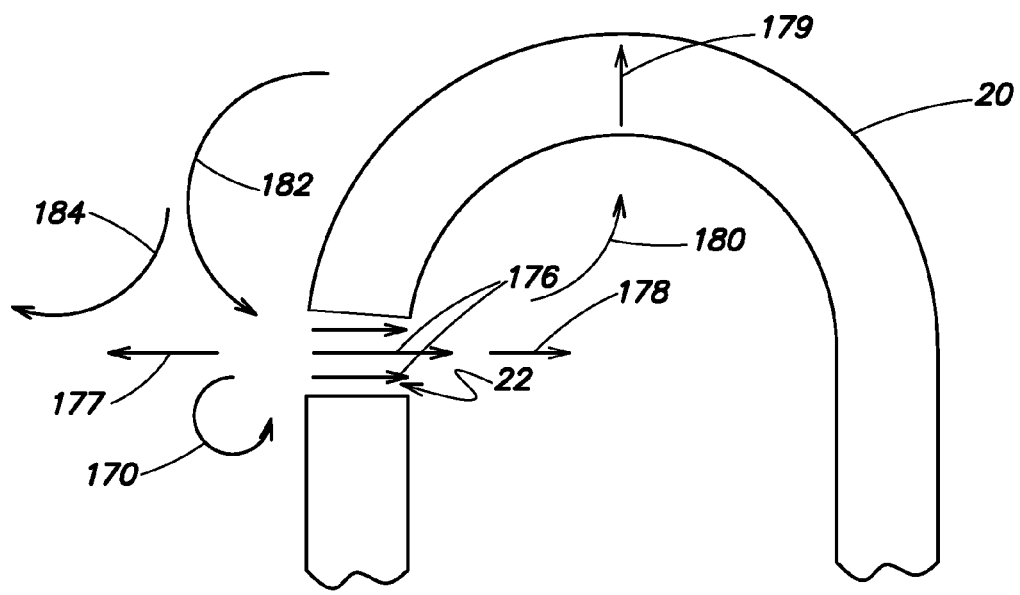

At reciprocating flow velocities for which the particle displacement inside the port in the reciprocating flow over a single cycle exceeds a significant fraction of the port diameter, the small amplitude assumption used in linear acoustics may be violated, and small inertial jets out of the port and toroidal recirculation flow cells around the axis of the port may form. This will occur at some point above the bi-directional flow threshold. These do not alter the basic exchange flow quantities, but result in slightly different flow distributions. FIGS. 17A-D illustrate the flow of tissue through the port 22 at different points in the longitudinal vibration of cannula 18. All of the flows illustrated disregard any aspiration pressure applied to cannula 18. FIG. 17A shows cannula 18 at maximum extension, resulting in simultaneously opposing port flows with little or no net flow through port 22. Lines 170 indicate recirculating flow outside of port 22, creating a small toroid around the port. Lines 172 indicate recirculating flow inside port 22. Lines 174 indicate flow exiting the port and line 176 indicates flow entering the port. Lines 177 and 178 are always present and indicate flow away from port 22 both inside and outside of the port. FIG. 17B shows cannula 18 at a point pulling back towards device 12 as indicated by arrow 171 with the net flow moving out of port 22. Lines 173 indicate flow back towards cannula 18. FIG. 17C shows cannula 18 at minimum extension, resulting in simultaneously opposing port flows with little or no net flow through port 22. FIG. 17D shows cannula 18 at a point moving forward away from device 12 as indicated by arrow 179 with the net flow moving into the port 22. Line 180 indicates the flow of fluid to fill the inside apex of cannula 18. Line 182 indicates the flow of fluid along the outer surface of cannula 18 into port 22. Line 184 indicates a toroid of flow away from the flow indicated at 182.

Larger tips have lower non-linear flow tip velocity thresholds than smaller tips for the same port area. The non-linear threshold changes rapidly with gauge and wall thickness. The non-linear threshold changes more slowly with changes in target aspiration rates. Also, the non-linear threshold tip velocity decreases in proportion to the port area.

At very high tip velocities, cavitation begins to develop on the outer surface of the tip. Vitreous may be liquefied externally, but the velocity or volume of the aspiration flow becomes much less predictable, acoustic field intensities become larger and less predictable, the fluid around the tip becomes more turbulent, acoustic streaming may develop, and the possibility of damage to adjacent tissues rises. This, then, may be considered as an upper limit for safe practice in using the devices and tips of the present disclosure. The velocity of the tip should be low enough that the pressure amplitude of a simple source equal to the difference between the inside and outside areas of the tip, minus the port area, is less than one atmosphere.

A quantitative understanding of this upper velocity threshold is as follow. In acoustics, it is known that for small point sources (of which the tips of the present disclosure are variants), $P=\rho*f*Q/(2r)$, where r is the radius from the acoustic center to the point under consideration. For the external surface of a tip, $Q=V_{tip}*A_{outer}$ and at the cavitation limit, P is one atmosphere or 103500 Pa. The equation is then $V_{tip}=(ATM/\rho)*(1/f)*(2r/A_{outer})$. For a linearly moving hemispherical shell, the acoustic center is located about ⅓ of a radius, or ⅙ of a diameter behind the apex of the shell on the axis of vibration, so that $r=r_{outer}/3$ or $D_{outer}/6$. The equation simplifies to $V_{tip}=(2ATM/\rho f)*((r_{outer}/3)/A_{outer})$. For tip velocities near to or above this, external cavitation is likely to occur.

It is important to note that the volume displaced by the portion of the outer surface that is matched by the inner area is part of the bi-directional or exchange flow, and may not contribute to the external cavitation, as it is being replaced by fluid coming through the port. Thus, $A_{outer}$ is the total outer area minus the total inner area (or, in the case of round geometry, $A_{outer}=(\pi/4)*(OD^2-ID^2)$. Thus, the limit is most strongly influenced by the tube wall thickness. Further note that the effective location of the acoustic center may shift because of this exchange, and make geometry factors much more difficult to calculate for a closed form equation. The limiting velocity for cavitation may be identified through FEA (finite element analysis) modeling of pressure fields around the vibrating tip and through direct observation with a high-speed camera looking for bubbles and voids. Note from the previous equation, that the external cavitation limit is relatively unaffected by the aspiration flow or the port area or location.

For some design conditions, reaching the optimal tip velocity for the bi-directional flow cannot be accomplished without exceeding the external cavitation threshold. In these instances, the tip should be vibrated close to but not above the external cavitation threshold for maximum effectiveness. This is particularly true for thicker walls, smaller gauges, and larger ports.

Summarizing the disclosure above: unidirectional flow domain is not effective; driving at levels above the unidirectional flow domain represents a lower bound of desirable drive levels; use of ultrasonic needles designed for cataract surgery (these normally do not have any inside tip surface area) in vitreous falls in this domain; these needles generally clog; for vitreous removal some non-zero tip velocity is required; this lower velocity limit may be defined by $V_{tip}>Q_{DF}/A_{InsideTip}$; bi-directional flow in the linear domain is effective, with effectiveness increasing as the amplitude of the bidirectional flow increases; bi-directional flow in the presence of internal cavitation or the is effective, but the increase in effectiveness is plateauing; bi-directional flow above the external cavitation threshold is no more effective in disrupting tissue at the port than the internally non-linear domain, while adverse effects such as turbulence and safety concerns start escalating rapidly. Propagation of shock waves from cavitation may disrupt either vitreous or retinal tissue indiscriminately in areas outside the immediate vicinity of the tip.

All the examples provided assume standard pressure at sea levels. At high elevations atmospheric pressure will be lower (for instance, about 80 kPa in Mexico City at 2200 meters or 7200 feet of elevation) and may alter some of the transition points, but not the basic principles. Operation at levels enough below sea level to significantly alter the performance is unlikely.

In addition, the device and needle performance will be affected by the distance between the port and the acoustic center of the external surface. As these two points move apart, the tip will move from the linear to the non-linear domain at lower tip velocities, because the action of the external surface will have less influence on the pressure at the port.

Although reference has been made to diameters such as inner diameters and outer diameters of the needle and the diameter of the port, the cross sectional areas can be non-circular without substantially affecting the basic principles.

Cavitation will start at around the vapor pressure of water for the ambient temperature; obviously, this is close to but greater than a full vacuum. We have assumed a full vacuum for the purposes of simplifying the analysis.

Some observations follow. The primary impact of the needle outer diameter (OD) is on the external cavitation velocity limit. The larger the OD, the greater the overall Q, even if wall thickness is maintained, although it is spread over a larger area. The most critical impact of the internal diameter(ID) of the needle is to the internal cavitation threshold—for a given port size, the larger the area, the lower the cavitation velocity threshold. Smaller ports increase the velocities through the port, for both aspiration and reciprocating flow. The velocity field outside the port will be generally independent of the port size, depending only on Q, at distances large with respect to the port. Port diameter has no effect on the lower unidirectional/bidirectional threshold or on the external cavitation bound. Wall thickness ((OD−ID)/2) influences the acoustic area and, if it is unchanged down the needle shaft, it influences the stiffness of the needle. The ratio of the ID to port diameter drives the velocity of the reciprocating flow. Large ratios (small ports near large IDs) make the velocity through the port large, starting the onset of bi-directional flow at lower strokes.

Some design considerations follow. Although the major factors that influence the balance of aspiration and bi-directional flow have been disclosed, the designer is likely to focus on the selection of the port area.

Absent any other effect, users have a strong preference for going through smaller incisions rather than larger incisions. However, they also want the highest flow possible, and stiff, reliable instruments, and they may have varying preferences for true end cutting action and visibility of tissue in front of the port.

The designer will select the largest outer diameter that will fit acceptably through the incision or through a cannula inserted through the incision.

The designer will select the inner diameter as large as possible (i.e. the thinnest wall thickness) without making the instrument unacceptably flexible or prone to breakage, in order to minimize flow resistance.

The designer typically prefers to use off the shelf materials for cost effectiveness, so they may further select their inner and outer diameters based on available dimensions for commodity medical grade micro-tubes.

The designer will select the angle between the port and the tip to balance the end cutting effect (at zero degrees) and port visibility when the tip is inserted (maximized at 90 degrees).

This leaves (to the designer) the selection of the port area and the tip velocity to provide optimal exchange flow according to the above equations, balanced against the selection of the tip velocity to minimize external cavitation, and the selection of the aspiration vacuum to achieve the desired aspiration flow.

Needle geometry (round or non-round), and tip geometry (hemispherical, bullet shaped, conical, flat, chisel, etc.) details may then be influenced by other user desires, or to enhance manufacturability or durability.

The substantially closed distal end of the needle contributes significantly to the liquefication of the vitreous. Open needles, such as standard phaco needles, do not have hydraulic gain and cannot create bi-directional flow. Furthermore, the ability to grab, hold onto and move a large chunk of tissue is highly desirable in phaco and fragmentation needles; traction is, essentially, desirable in phaco procedures, and undesirable in vitrectomy procedures. Phaco needles have evolved bell structures with large open cross-sectional areas specifically intended to enhance purchase (the amount of pulling or holding force available). Since the area of the single port in standard phaco needles is equal to or larger than the aspiration cross-section area, any pieces that do get broken up barely fit through the subsequent aspiration area, and can get bound together, causing the clogs that are seen clinically.

The effect of vitreous liquefication might be observed by two separate methods.

Method Ia: In this method, a fixed volume of either pure vitreous or pure water is aspirated out of an eye with a fixed vacuum, and the time to aspirate the tissue is measured. When the times for the two different fluids are significantly different, the tissue is much less liquid than the water (i.e. more viscous); where they approach each other, the tissue is substantially liquid. This measurement can be made on a comparative basis, comparing mechanical cutters and ultrasonic technologies.

Method Ib: A variant of method Ia aspirates a volume of either pure vitreous or pure water with a fixed vacuum for a fixed time; in this case, the device that permits the greatest volume or mass of aspiration in the fixed time is superior, and aspirating a similar mass or volume as can be aspirated using pure water is an indication that the tissue is substantially liquid.

Method II: Samples of vitreous are cut or liquefied, and the molecular weight of both the pre and post processed tissue is measured and compared to that of water. Molecular weight is a critical mechanical characteristic of a medium, and relates to a number of properties, including fluidity. In this case, lower molecular weights reflect greater liquidity.

A variety of approaches may be taken to making the devices of the example embodiments, which will affect aspects of the geometry not critical to the aims of the vitreous removal.

For instance, the devices may be machined monolithically out of a material such as Titanium. In this case, the inner path is formed by drilling a blind hole into a titanium rod. Since the point of the drill will typically not be hemispherical, the inner surface of the end will not be hemispherical, so the shape and thickness of the closed end may be non-uniform. However, in this case, the holes drilled in the closed end will still have a cross-sectional area smaller than the area of the aspiration path through the device.

The holes may be fabricated by a variety of methods, including but not limited to punching, drilling, or cut using a wire EDM process.

The shaft may be formed by deep drawing, machining monolithically, or sealing preformed, precut micro-tubes with welding, swaging or other processes.

Also, the tip with a port may be formed separately from the shaft of the needle and attached by any known method such as adhesive, welding, frictional contact, or any other method that secures the tip and the shaft to each other. In such a two-part design where the ID of the shaft is smaller than the ID of the tip portion the ID of the shaft is the ID to be used in the teachings above.

The devices may be constructed so that the user receives both the cutting needle and the ultrasonic driver, or the needles may be made so that they can be installed on a reusable ultrasonic driver by the user.

The devices may be constructed out of any bio-compatible material that is appropriate for the fabrication process, including metals and plastics.

One example that was constructed was a 22 gauge needle with four 0.005" ports, in combination with a 150 mmHg port pressure differential, driven at velocities of up to about 3 m/sec (35 microns peak to peak at 28.5 kHz), resulting in water flow rates around 10 ml/min and vitreous flow rates around 2.5 to 4.0 ml/min. The lumen ID was around 0.020", and the nominal port fluid velocity was less than $((20/10)^2*3=)$ 12 m/sec, well above the 6 m/sec maximum achievable water aspiration flow from the pressure differential, or the 0.8 m/sec vitreous aspiration flow velocity expected for a 2.5 ml/min flow through the four ports. At the higher velocities, internal cavitation was starting to take place. The relative liquidity of the vitreous is apparent from the fact that vitreous and water flow rates were less than an order of magnitude apart.

Other configurations can be imagined. As the total port area gets larger, total aspiration volume increases for a fixed pressure differential; ultimately, the desire to maintain a stable eye (and, to a lesser extent, a firm eye) dominates the design decision process. As the infusion cannulas get smaller (for instance, with 25 gauge or 27 gauge cannulas), the drop in eye pressure from peak water infusion flow becomes increasingly important, and the overall optimal design begins to converge on the small port/high vacuum design identified earlier.

In conventional guillotine cutters, the vitreous is cut in to segments using a scissor action between two opposing metallic surfaces; the segments are relatively large (for instance, approximately 0.2 µl per segment for a 5000 CPM cutter aspirating 1 ml of processed vitreous per minute).

In contrast, in the example embodiments, vitreous may be liquefied through a combination of highly localized shear and compressive forces by the needle, resulting in much smaller segments between individual processing stress points (for instance, less than 0.0006 µl per segment for a 28.5 kHz device aspirating 1 ml of vitreous per minute).

The following is an outline of the process of liquefying vitreous using the example embodiments:
1) Bi-directional flow stresses and breaks the vitreous strands
2) Relatively high velocity flow through small ports results in non-constant flow velocity profiles, classically considered to be parabolic, resulting in high shearing forces through the flow
3) The material passing through the port undergoes cyclical pressure cycles with a minimum rarifying vacuum potentially as low as the vapor pressure of water at body temperature (around 7000 Pa, absolute) and a maximum compressive pressure several atmospheres, which will cause any trapped gas to expand and compress quickly, causing local disruption
4) The material flowing past the edges of the port will be forced to turn ninety degrees suddenly, undergoing high vorticity, which will also require large but highly localized shearing forces, and
5) The material at the external edge of the ports will be subjected to a shearing shock wave by the edge of the port at the forward and rearward most extreme needle position during each cycle of the stroke, creating many points for tearing, and
6) Toroidal flow cells around the axis of the ports at the inside and outside at higher velocities may tear material apart.

Figure 18:
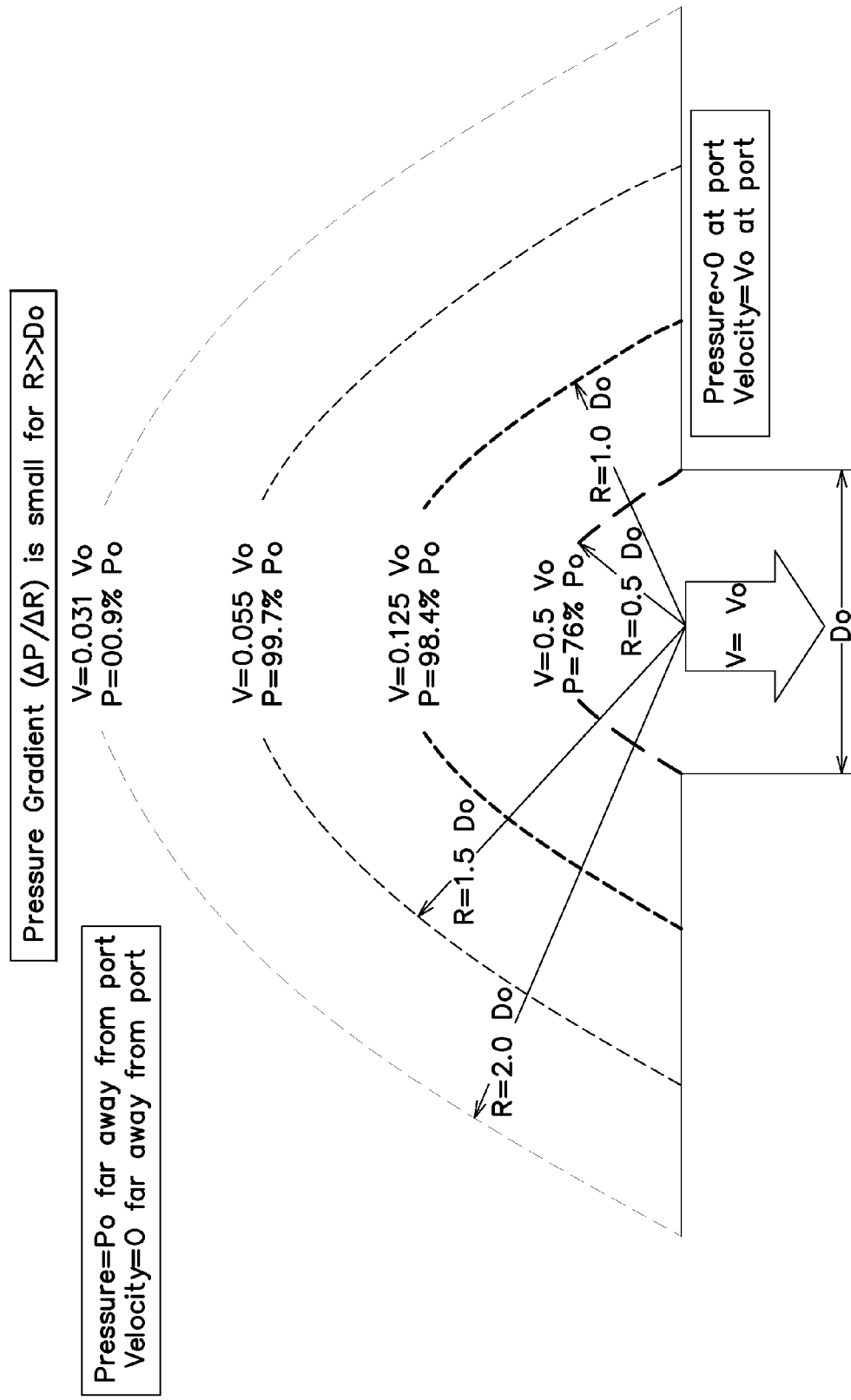
FIG. 18 is a diagram showing the pressure gradient drop as a function of a distance from the port.

The example embodiments control traction through use of relatively small port openings, compared to conventional ultrasonic emulsification devices. It can be shown that on a first order basis, pressure gradients drop dramatically as distance from the port increases, and the pressure drop between distant points and points about one diameter from the port is only around 1.5% of the total pressure drop from the distant field to the port itself (see FIG. 18). Guillotine ports of mechanical vit cutters must be large—close to size of the OD of the outer needle, or around 0.025" (635 microns) for a 23 gauge needle—in order to permit the vitreous to enter the port far enough to get trapped between the moving inner needle and the front edge of the outer port to be cut, and in order to ensure that enough vitreous is cut each cut cycle to create useful flow. Because of the localized shearing action of the ultrasonic vitrectomy tip and the significantly higher cycle rate, vitreous can still travel far enough into small ports to be cut at clinically useful rates.

Conventional ultrasonic needles generally have a single large diameter distally located end port, made as large as possible to improve the traction (also referred to as "purchase" in cataract surgery) that can be applied to lens fragments in order to move them around. Post-phaco Irrigation/Aspiration (I/A) tips are known with ports as small as 0.3 mm (0.012").

The example embodiments also control traction by the basic vitreous cutting action, which creates small ruptures in the vitreous at the entrance to the port and breaks up the fibers in the vitreous near the edge, so that they cannot create localize pulling action along the length of the strand.

The example embodiments also control traction by enabling the use of relatively low vacuum levels.

Figure 19:
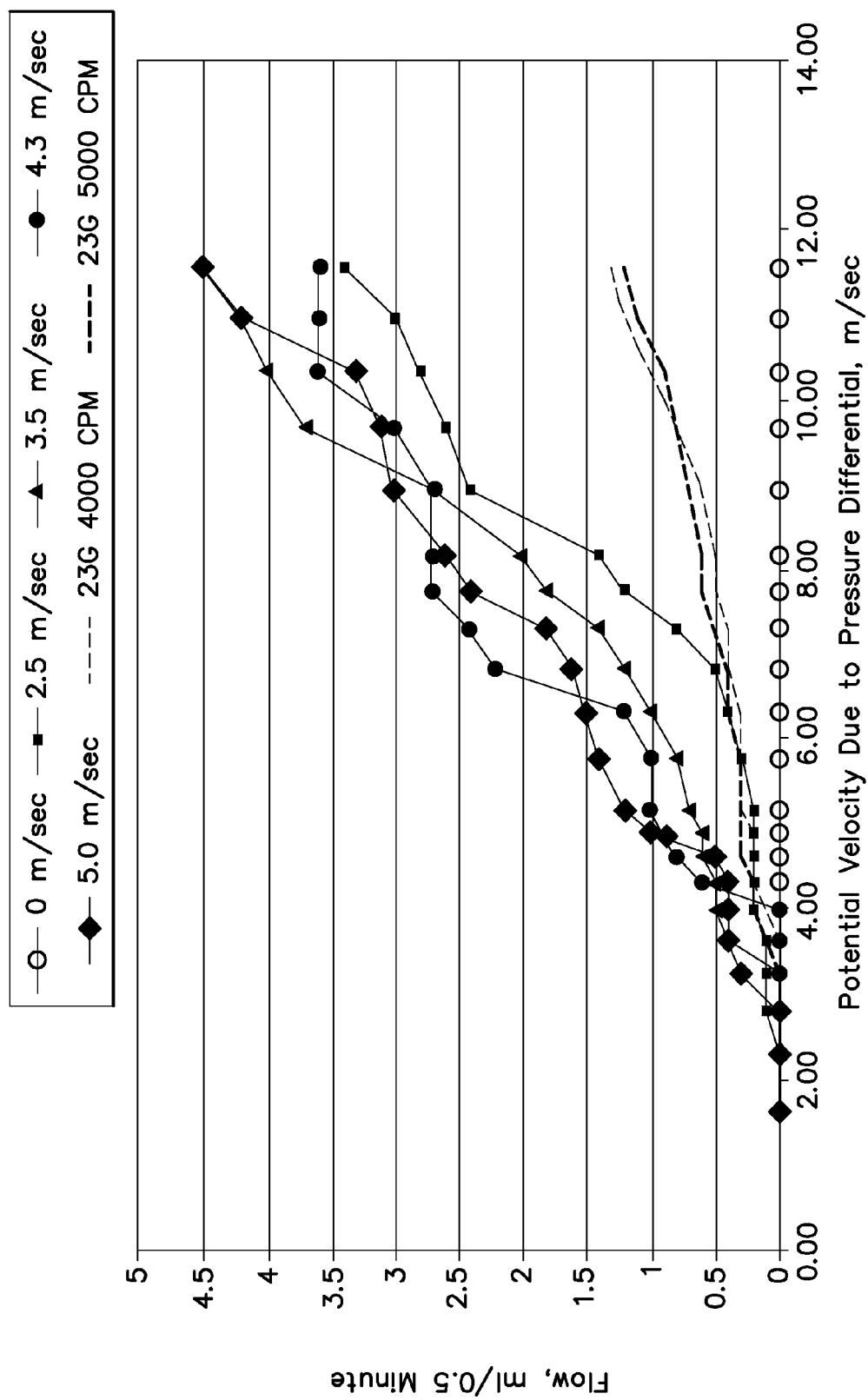
FIG. 19 is a graph showing vitreous flow rates of a 22 gauge cannula.

FIG. 19 is a graph showing the vitreous flow rates (Flow, on y-axis) of the 22 gauge cannula with 4 ports of 0.005" diameter (127 microns) described above, for a given potential maximum flow velocity of water (Potential Velocity, on x-axis) at various ultrasonic power levels of a Stellaris® (available from Bausch & Lomb Incorporated) phacoemulsification device (the ultrasonic levels are expressed in terms of peak tip velocity in m/sec).

Any flow out of the eye must be balanced by flow into the eye through an infusion cannula. The flow device may be aspirating any fluid in the eye, including infusion solution (water/BSS). The pressure used to supply this fluid is generally kept low (as close to the healthy eye intraocular pressure (IOP) of less than 22 mm HG as possible). For low viscosity flow out of the eye, the pressure drop across the infusion cannula causes a pressure drop within the eye; if the pressure drops too far, harm can result to the eye. Typical cannulas for 23 gauge surgery can have 6 to 10 mm of pressure drop from just 10 ml/min of infusion flow. In sample needles, vitreous flow rates have been around 33% of water flow rates, some times as high as 40% of water flow rates, and vitreous aspiration rates of 1 to 2 ml/min permit bulk removal of all the vitreous in the eye in a minute or two, which has been clinically acceptable. Therefore, ports designed to permit (for instance) 10 ml/min of water flow through the needle at the anticipated pressure differential level may be considered large enough, and larger ones do not need to be used.

Kits with larger infusion cannulas and smaller vitrectomy cannulas could help offset this somewhat, but there will always be some upper limit to flow based on infusion limits with a passive infusion scheme. An active scheme, which detects flow and increases IOP, can also offset this, but carries performance risk and cost and, given the acceptable performance achievable with passive systems and the vitrectomy needle, this may be avoided.

Ports smaller than those found on known phacoemulsification or fragmentation needles perform better for several reasons. First, smaller ports increase the velocity of the flow through the port, creating bi-directional flow at lower velocities compared to larger ports. Secondly, they significantly reduce the static traction, (see FIG. 20 and discussion below). Thirdly, small ports are a boundary protecting the high flow field from the tip, permitting the tip to be used closer to the retina.

Figure 20:
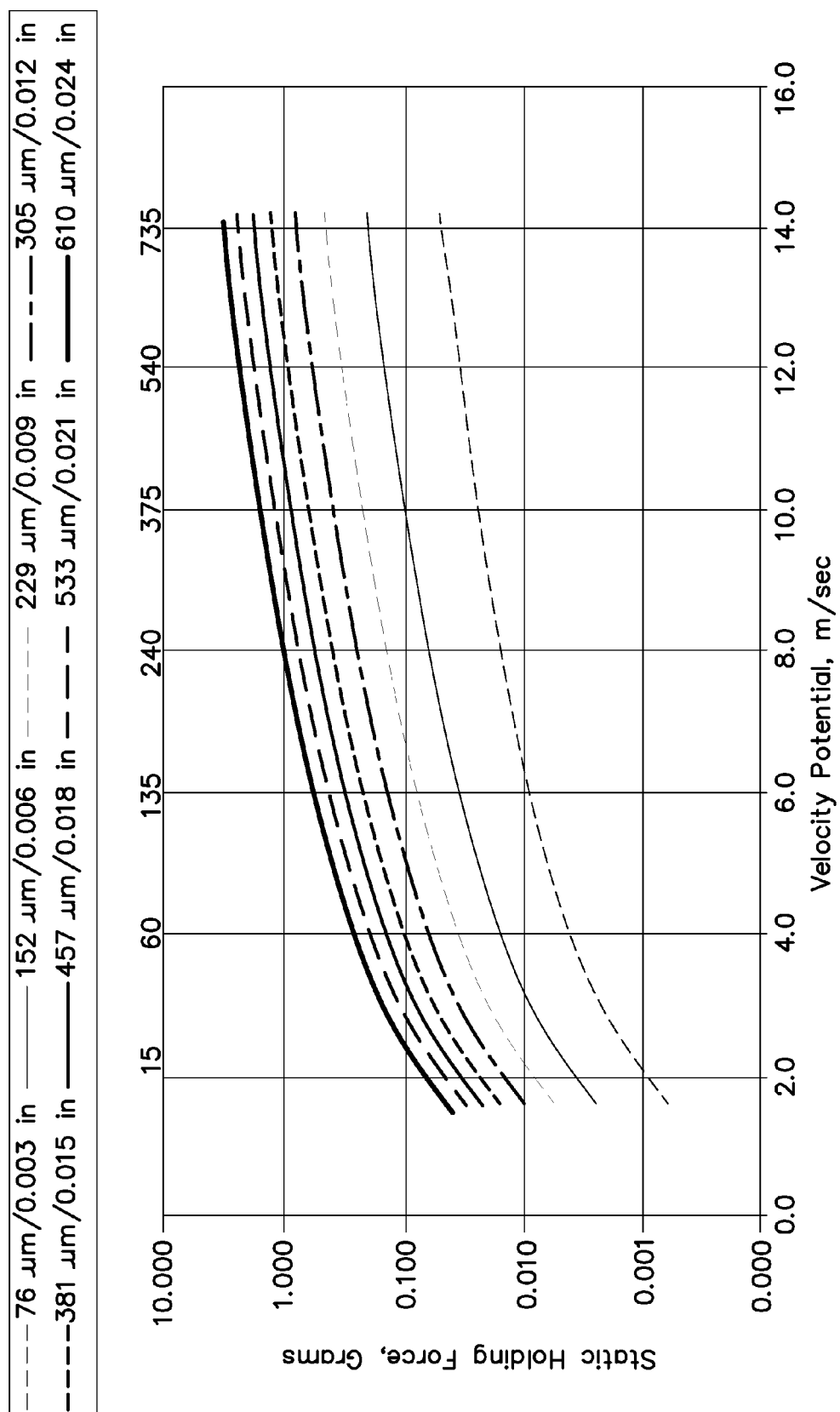
FIG. 20 is a graph showing static holding forces of various ports sizes.

FIG. 20 is a graph showing the different gram holding strengths (in a log scale on the y-axis) of various port sizes at different velocity potentials. A conventional 23 gauge vit cutter might have port on the order of 0.018" to 0.024", resulting in around 1.5 ml/min of vitreous flow at around 350 mm Hg vacuum, generating a gram or more of static traction. In contrast, 22 gauge samples built with four 0.005" holes (equivalent to one 0.010" hole) provided the same flow at around 150 mm Hg, and would generate only about 100 milligrams of traction. Orders of magnitude less holding force, is most likely why the example embodiments provide superior vitreous removal without any notable traction compared to conventional mechanical vit cutters.

Standard phaco or frag needles are not effective for vitreous removal for at least a few reasons. Chief among these is that they have no structure to generate reciprocating flow into and out of the port at the point of contact with the vitreous. This results in large tangles of vitreous dragging on the walls at the entrance, clogging the port and creating external traction. Furthermore, the flow limiting diameter has typically been located all along the shaft, and, where smaller diameters have been used, a bell has been located at the distal end, to provide better traction for lens material, further reducing the aspiration fluid velocity at the port where the vibration is taking place. Furthermore, the larger port diameters would permit some aspiration of vitreous, albeit with traction, encouraging users to use minimal aspiration vacuum levels, further limiting aspiration fluid velocities. The present examples requires some vibration, to start the fluid through the ports, but the smaller ports result in higher fluid velocities, permitting lower velocity tip motion, which limits external cavitation.

A chop needle was designed with a constrictive throat near the hub of the needle. Although this has a smaller aspiration port that would create higher flow rates, it is not located distally, where the vibratory motion first interacts with the tip. At the entry port, the diameter is much larger (to enhance purchase, as the chop needle is intended for lens removal and manipulation), decreasing the aspiration velocities.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

We claim:

1. An ophthalmic surgical device comprising:
a housing having a distal end and a proximal end;
a cannula attached to the housing distal end and having a distal tip with at least one port in communication with a lumen extending through the cannula and in communication with an aspiration path in the housing and wherein a cross-sectional area of the port is less than a cross-sectional area of the lumen;
a vibration source held within the housing for vibrating the distal tip of the cannula for assisting in vitreous and other tissue removal from a patient's eye;
an aspiration source connected to the aspiration path for applying a negative pressure to the lumen and the at least one port for removing fluids and the vitreous and other tissue from the eye; and
wherein the vibration source and the aspiration source together create a periodic bi-directional flow of the vitreous and other tissue through the port during aspiration without creating cavitation externally of the distal tip.

2. The device of claim 1 wherein the housing and the vibration source are a part of a phacoemulsification surgical instrument.

3. The device of claim 2 wherein the cannula has a threaded connection for attachment to the phacoemulsification surgical instrument.

4. The device of claim 1 further including a guard device attached to the cannula and extending beyond the cannula distal tip.

5. The device of claim 1 further including a jacket attached to the device and surrounding and extending beyond the cannula distal tip, wherein the jacket includes a port proximate the cannula distal tip.

6. The device of claim 1 wherein the cannula distal tip includes multiple ports in communication with the lumen.

7. The device of claim 6 wherein the multiple ports are formed to a side of a central axis of the cannula.

8. The device of claim 1 wherein the at least one port is formed to a side of the cannula distal tip to assist a surgeon to see the at least one port during surgery and to allow a side of the cannula distal tip opposite the side with the at least one port to contact delicate tissue without damaging the tissue.

9. The device of claim 1 wherein the at least one port has a cross-sectional area less than approximately 75,000 square microns ($\mu m^2$).

10. The device of claim 1 wherein the at least one port has a cross-sectional area less than approximately 35,000 square microns ($\mu m^2$).

11. The device of claim 1 wherein the at least one port has a cross-sectional area less than approximately 20,000 square microns ($\mu m^2$).

12. The device of claim 1 wherein the vibration source causes the cannula distal tip to vibrate in one or more of a longitudinal manner, a torsional manner, and a transverse manner.

13. The device of claim 1 wherein the vibration source vibrates the cannula distal tip to vibrate sufficiently to remove a lens fragment.

14. The device of claim 1 wherein the cannula is curved to assist a surgeon to see the at least one port.

15. The device of claim 1 wherein the at least one port has a holding force of less than 1 gram at 735 millimeters of mercury (mmHg) vacuum or less.

16. The device of claim 1 further including an infusion fluid source in communication with the eye and wherein a pressure of infusion fluid into the eye forms a part of the intraocular pressure.

17. The device of claim 16 further including an infusion cannula for insertion into the eye and having a cross-sectional area larger than the cross-sectional area of the lumen.

18. The device of claim 1 wherein the vibration source and the aspiration source together create a desired aspiration flow rate of tissue through the port and the lumen.

19. The device of claim 1 wherein the cannula is vibrated at approximately 14.4 meters/second multiplied by a ratio of the port cross-sectional area to the lumen cross-sectional area.

20. The device of claim 1 wherein the cannula has an outer diameter of 23 gauge or smaller.

21. The device of claim 1 wherein the port cross-sectional area is less than ⅓ of the lumen cross-sectional area.

* * * * *